(12) United States Patent
Fujita et al.

(10) Patent No.: US 9,358,159 B2
(45) Date of Patent: Jun. 7, 2016

(54) ULTRASONIC WELDING DEVICE AND METHOD OF PRODUCING DISPOSABLE DIAPER USING SAME

(71) Applicant: ZUIKO CORPORATION, Settsu-shi, Osaka (JP)

(72) Inventors: Yukihiko Fujita, Osaka (JP); Hideyuki Nakamura, Osaka (JP)

(73) Assignee: Zuiko Corporation (JP)

( * ) Notice: Subject to any disclaimer, the term of this patent is extended or adjusted under 35 U.S.C. 154(b) by 0 days.

(21) Appl. No.: 14/893,667

(22) PCT Filed: Jun. 13, 2014

(86) PCT No.: PCT/JP2014/065808
§ 371 (c)(1),
(2) Date: Nov. 24, 2015

(87) PCT Pub. No.: WO2014/200104
PCT Pub. Date: Dec. 18, 2014

(65) Prior Publication Data
US 2016/0100990 A1    Apr. 14, 2016

(30) Foreign Application Priority Data

Jun. 14, 2013  (JP) ................................ 2013-125943

(51) Int. Cl.
| | | |
|---|---|---|
| B32B 37/00 | (2006.01) | |
| A61F 13/15 | (2006.01) | |
| B29C 65/74 | (2006.01) | |
| B29C 65/08 | (2006.01) | |
| B29C 65/78 | (2006.01) | |
| B29L 31/48 | (2006.01) | |

(52) U.S. Cl.
CPC .......... *A61F 13/15585* (2013.01); *B29C 65/086* (2013.01); *B29C 65/747* (2013.01); *B29C 65/7885* (2013.01); *B29L 2031/4878* (2013.01)

(58) Field of Classification Search
CPC .... B29C 65/08; B29C 65/083; B29C 65/086; B29C 65/087; B29C 65/088; B29C 65/7885; B29C 65/747; B29C 66/0326; B29C 66/81431; A61F 13/15585
USPC .................................. 156/73.1, 580.1, 580.2
See application file for complete search history.

(56) References Cited

U.S. PATENT DOCUMENTS

| | | | |
|---|---|---|---|
| 4,758,293 A | 7/1988 | Samida | |
| 5,660,679 A | 8/1997 | Rajala et al. | |
| 5,667,608 A | 9/1997 | Rajala et al. | |
| 7,383,865 B2 * | 6/2008 | Umebayashi | ..... A61F 13/15739 156/350 |

(Continued)

FOREIGN PATENT DOCUMENTS

| | | |
|---|---|---|
| JP | 3988835 | 7/2007 |
| JP | 2012-76343 | 4/2012 |

OTHER PUBLICATIONS

International Search Report.

*Primary Examiner* — James Sells
(74) *Attorney, Agent, or Firm* — Gerald Hespos; Michael Porco; Matthew Hespos

(57) ABSTRACT

The displacement mechanism includes: an urging mechanism that urges an anvil roller toward an ultrasonic horn in such a manner that output surfaces and a welding surface move closer in the normal direction thereof; and a pressed member that has guide surfaces against which the outer surface of the anvil roller, positioned within non-welding areas, are pressed by an urging force of the urging mechanism, the pressed member being fixed to a sheet holding roller in a state where a pressed surface is disposed within the width-direction range of a slit. In response to the movement of the anvil roller from a welding area to the non-welding areas, the guide surfaces of the pressed member guide the anvil roller in a direction in which the output surfaces and the welding surface move away from each other.

9 Claims, 12 Drawing Sheets

(56) References Cited

U.S. PATENT DOCUMENTS 7,449,084 B2 * 11/2008 Nakakado ......... A61F 13/15739 156/580.1
7,658,053 B2 * 2/2010 Honegger ............... B29C 65/02 53/374.5
9,186,845 B2 * 11/2015 Shimada ............ A61F 13/15739
2013/0174965 A1 7/2013 Yamamoto et al.

* cited by examiner

ULTRASONIC WELDING DEVICE AND METHOD OF PRODUCING DISPOSABLE DIAPER USING SAME

TECHNICAL FIELD

The present invention relates to an ultrasonic welding device for ultrasonically welding an object to be welded, and to a method of producing a disposable diaper using the ultrasonic welding device.

BACKGROUND ART

Conventional ultrasonic welding devices include ultrasonic welding devices each provided with an anvil and an ultrasonic horn, wherein an object to be welded is sandwiched between the anvil and the ultrasonic horn, and in that state, ultrasonic vibration is applied to the ultrasonic horn, to weld as a result the object to be welded.

Known instances of such ultrasonic welding devices include a device that is provided with a holding member that holds an object to be welded, and an anvil roller that can move with respect to the holding member, between a welding area over which the object to be welded is welded between the ultrasonic horn and the anvil roller at a position where the anvil roller overlaps, in a plan view, with the object to be welded that is held on the holding member, and a non-welding area, across the object to be welded (see, for instance, Japanese Patent Application Publication No. 2012-76343).

In order to weld the object to be welded, it is necessary to bring the anvil roller close to the ultrasonic horn, at a region at which the object to be welded is present between the anvil roller and the ultrasonic horn, within the range of movement of the anvil roller. Conversely, it is necessary to draw the anvil away from the ultrasonic horn in order to suppress wear and degradation of the anvil roller and the ultrasonic horn, at a region at which the object to be welded is not present between the anvil roller and the ultrasonic horn, within the range of movement of the anvil roller.

The ultrasonic welding device disclosed in Japanese Patent Application Publication No. 2012-76343, therefore, has a driving mechanism for driving the anvil roller with respect to the ultrasonic horn in such a manner that the anvil roller approaches the ultrasonic horn in the welding area, and moves away from the ultrasonic horn in the non-welding area.

FIG. 14 is a side-view diagram illustrating the schematic configuration of a driving mechanism of the ultrasonic welding device disclosed in Japanese Patent Application Publication No. 2012-76343.

The driving mechanism disclosed in Japanese Patent Application Publication No. 2012-76343 is provided with: a horn holding member 103 that holds an ultrasonic horn 100; an anvil holding member 104 that is pivotably mounted on the horn holding member 103 about a pivot shaft 104a, and that holds an anvil roller 101 rotatably about a rotary shaft 101a; and a cylinder 105 that swings the anvil holding member 104 with respect to the horn holding member 103.

As illustrated in FIG. 14, the cylinder 105 contracts in such a manner that the anvil roller 101 moves away from the ultrasonic horn 100, in a state where anvil roller 101 has moved to a non-welding area across the object to be welded 106.

As illustrated in FIG. 15, the cylinder 105 extends in such a manner that the anvil roller 101 moves close to the ultrasonic horn 100, in a welding area over which the object to be welded 106 is welded.

In the driving mechanism disclosed in Japanese Patent Application Publication No. 2012-76343, however, the anvil roller 101 is caused to move close to or away from the ultrasonic horn 100 through extension and contraction of the cylinder 105, and, accordingly, both the cylinder 105 and a structure for powering the same are necessary herein, which causes a size of the ultrasonic welding device into larger. Further, complex driving control of the cylinder 105 is required in order to move the anvil roller 101 close to or away from the ultrasonic horn 100 in response to the movement between the welding area and the non-welding area.

SUMMARY OF INVENTION

It is an object of the present invention to provide an ultrasonic welding device that allows simplifying the configuration and control for causing an ultrasonic horn and an anvil approach each other and move away from each other, and to provide a method of producing a disposable diaper using the ultrasonic welding device.

In order to solve the above problem, the present invention provides an ultrasonic welding device for ultrasonically welding an object to be welded, the ultrasonic welding device including: a holding member that holds an object to be welded; a pair of welding tools having an ultrasonic horn that has an output surface that applies ultrasonic vibration to the object to be welded, and an anvil having a welding surface over which the object to be welded is welded between the output surface of the ultrasonic horn and the anvil the pair of welding tools being configured such that a moving welding tool that is one of the pair of welding tools can move, with respect to the holding member, over a welding area at which the output surface or the welding surface of the moving welding tool overlaps, in a plan view, the object to be welded that is held by the holding member, and over which the object to be welded is welded between the moving welding tool and a counterpart welding tool that is the other of the pair of welding tools, and a non-welding area that is spaced from the welding area in a plan view; and a displacement mechanism that displaces the moving welding tool with respect to the counterpart welding tool, in such a manner that the output surface and the welding surface approach each other in the welding area, and the output surface and the welding surface move away from each other in the non-welding area, wherein an end section of the counterpart welding tool including the output surface or the welding surface is branched, in a direction perpendicular to a movement direction of the moving welding tool, by a slit that extends in the movement direction, and has a pair of end faces positioned on both sides of the slit and functioning as the output surface or the welding surface, the displacement mechanism includes an urging mechanism that urges the moving welding tool toward the counterpart welding tool, in such a manner that the output surface and the welding surface move closer in the normal direction thereof, and a pressed member that has a pressed surface against which an outer surface of the moving welding tool, positioned within the non-welding area, is pressed by an urging force of the urging mechanism, the pressed member being fixed to the holding member in a state where the pressed surface is disposed within a width-direction range of the slit, and at least one of the pressed surface of the pressed member and the outer surface of the moving welding tool functions as a guide surface which, in response to the movement of the moving welding tool from the welding area to the non-welding area, guides the moving welding tool in a direction in which the output surface and the welding surface move away from each other.

Further, the present invention provides a method of producing a disposable diaper using the above ultrasonic welding device, the disposable diaper having a front abdominal section disposed on the abdomen of a wearer, a rear dorsal section disposed on the buttocks of the wearer, and a crotch section that extends from the front abdominal section, passing between the legs of the wearer, up to the rear dorsal section, the method having: a preparation step of preparing a continuous body in which constituent elements each constituted by connecting the front abdominal section and the rear dorsal section via the crotch section in a longitudinal direction are continuous in a transversal direction; a fold-in-half step of folding in half the continuous body in the longitudinal direction; a welding step of moving the moving welding tool over the welding area and the non-welding area and inputting ultrasonic vibration to the ultrasonic horn, to simultaneously weld two sites of an overlap portion in which a portion corresponding to a side edge portion of the front abdominal section and a portion corresponding to a side edge portion of the rear dorsal section are overlapped each other, in the continuous body, between a pair of end faces of the counterpart welding tool and an output surface or a welding surface of the moving welding tool; and a cutting step of cutting the continuous body between two weld sections formed in the welding step.

The present invention allows simplifying the configuration and control for causing an ultrasonic horn and an anvil approach each other and move away from each other.

DESCRIPTION OF EMBODIMENTS

The embodiments of the present invention are described hereinbelow by referring to the attached figures. The following embodiments are examples substantiating the present invention and do not limit the technical scope of the present invention.

Figure 1:
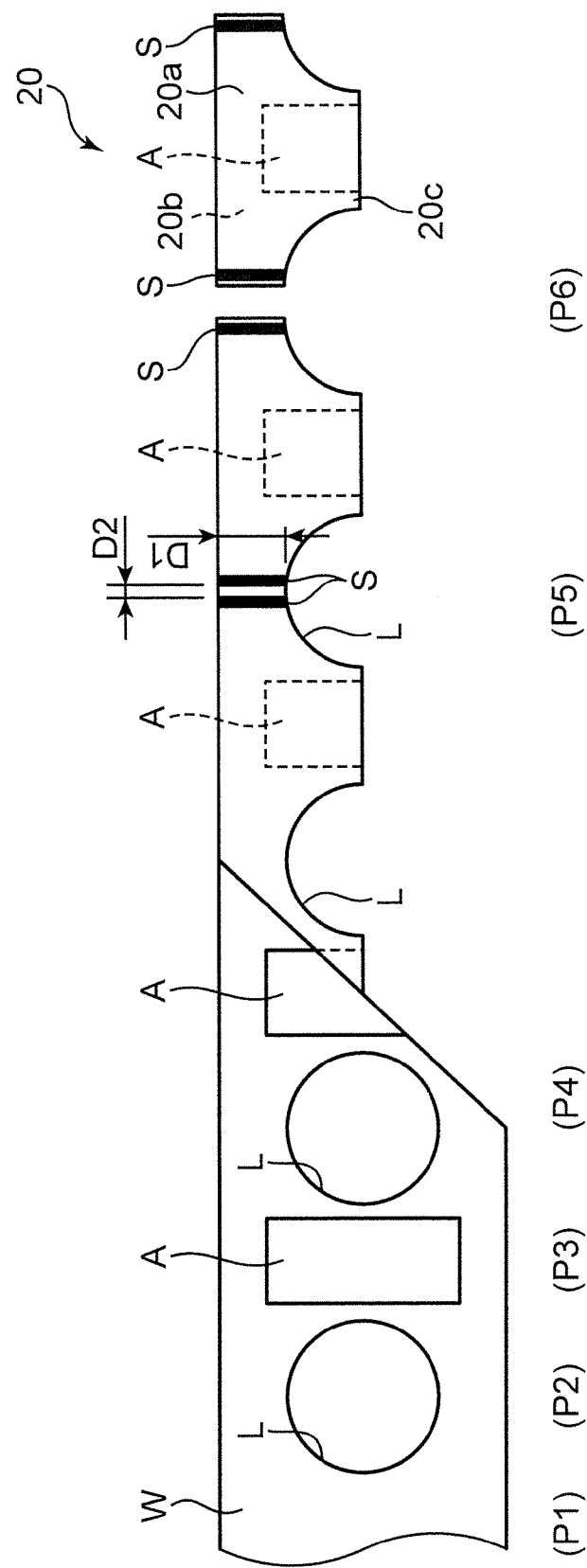
FIG. 1 is a process diagram for explaining a method of producing a disposable diaper according to the present invention.

With reference to FIG. 1, a disposable diaper 20 includes, when worn, a front abdominal section 20a disposed on the abdomen of a wearer, a rear dorsal section 20b disposed on the buttocks of the wearer, and a crotch section 20c that extends from the front abdominal section 20a, passing between the legs of the wearer, up to the rear dorsal section 20b.

Both side edge portions of the front abdominal section 20a and both side edge portions of the rear dorsal section 20b are welded to each other by two weld sections S, in such a manner that the front abdominal section 20a and the rear dorsal section 20b are connected in the form of a ring.

A method of producing the disposable diaper 20 will be explained next.

<Transport Step P1>

In the transport step P1, a sheet W that extends in a specific direction is transported along the length direction of the sheet W. In the explanation hereafter, the flow direction of the sheet W will be referred to as transversal direction, and the direction perpendicular to the transversal direction in FIG. 1 will be referred to as longitudinal direction.

The sheet W has an inner sheet that faces the body surface of the wearer when the wearer wears the diaper, an outer sheet that faces away from the wearer when the wearer wears the diaper, and an elastic member that is sandwiched between the inner sheet and the outer sheet.

The inner sheet is constituted by a nonwoven fabric sheet and/or a mesh sheet having liquid permeability. The outer sheet is constituted by a material, identical to that of the inner sheet, a polyethylene film, a polypropylene film, or a nonwoven fabric having water repellency and breathability.

The elastic member is constituted by a sheet or thread made of polyurethane, natural rubber, or a thermoplastic resin.

<Leg Hole Forming Step P2>

In the leg hole forming step P2, leg holes L are formed at a central position of the sheet W in the longitudinal direction.

Each region between the two leg holes L in the sheet W is a portion corresponding to the crotch section 20c. The positions on both sides of each portion in the sheet W corresponding to the crotch section 20c, in the longitudinal direction, correspond herein to the front abdominal section 20a and the rear dorsal section 20b, respectively.

That is, the transport step P1 and the leg hole forming step P2 correspond to the preparation step of preparing a continuous body in which constituent elements each constituted by connecting the front abdominal section 20a and the rear dorsal section 20b via the crotch section 20c in the longitudinal direction are continuous in the transversal direction.

<Absorbent Body Bonding Step P3>

In the absorbent body bonding step P3, an absorbent body A is bonded at a position in the sheet W between the two leg holes L.

The absorbent body A includes a permeable sheet having liquid permeability, a water-repellent sheet having water-repellency and breathability, and an absorbent core sandwiched between the permeable sheet and the water-repellent sheet.

The permeable sheet is constituted by a nonwoven fabric sheet and/or a mesh sheet having liquid permeability. The water-repellent sheet is constituted by a polyethylene film, a polypropylene film, or a nonwoven fabric having water-repellency and breathability.

The absorbent core is molded through layering of crushed pulp or crushed pulp mixed with a high water-absorbing polymer.

A method is explained herein where the absorbent body A is bonded to the sheet W, but the absorbent core may be bonded in a state where the absorbent core is sandwiched between the inner sheet and the outer sheet of the sheet W. In this case, the inner sheet is constituted by a nonwoven fabric sheet and/or a mesh sheet having liquid permeability. The outer sheet is constituted by a polyethylene film, a polypropylene film, or a nonwoven fabric having water-repellency and breathability.

<Fold-in-Half Step P4>

In the fold-in-half step P4, the sheet W (continuous body) having the absorbent body A placed thereon is folded in half in the longitudinal direction. As a result, the portion of the sheet W corresponding to the front abdominal section 20a and the portion corresponding to the rear dorsal section 20b are overlapped each other.

<Welding Step P5>

In the welding step P5, a portion of the folded sheet W corresponding to a side edge portion of the front abdominal section 20a and the portion corresponding to a side edge portion of the rear dorsal section 20b are ultrasonically welded.

In the welding step P5, specifically, two sites of the sheet W are ultrasonically welded simultaneously, with a spacing D2 including a predetermined cutting range as a range of cutting in the cutting step P6 described below.

The two weld sections S are respectively formed over a welding range D1 in the longitudinal direction of a portion corresponding to a side edge portion of the front abdominal section 20a, and a portion corresponding to a side edge portion of the rear dorsal section 20b.

<Cutting Step P6>

In the cutting step P6, the sheet W is cut along a respective cutting line that extends, in the longitudinal direction, between two weld sections S formed in the welding step P5. The sheet W (continuous body) is cut as a result into each disposable diaper 20.

First Embodiment

Figure 2:
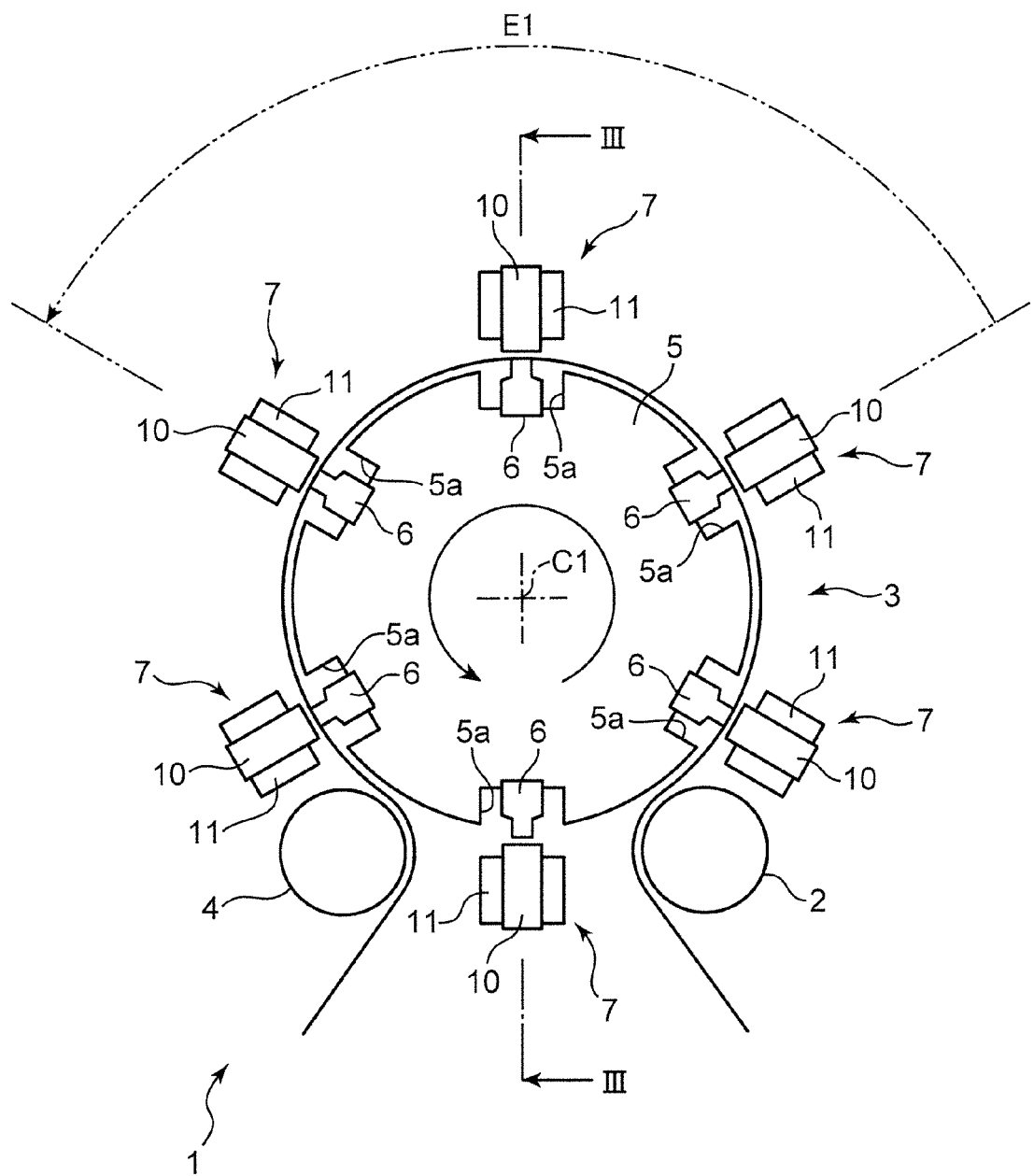
FIG. 2 is a front-view diagram illustrating the schematic configuration of an ultrasonic welding device according to a first embodiment of the present invention, for carrying out the welding step illustrated in FIG. 1.

With reference to FIG. 2, an explanation follows next on an ultrasonic welding device 1, according to the first embodiment, that carries out the welding step P5.

The ultrasonic welding device 1 is provided with an introduction roller 2 that introduces the folded sheet W undergone the fold-in-half step P4, a welding drum 3 that welds the sheet W that is introduced by the introduction roller 2, and a lead-out roller 4 that leads out the sheet W welded by the welding drum 3.

The welding drum 3 is provided with: a sheet holding drum (holding member) 5 that holds the sheet W that is introduced by the introduction roller 2; six ultrasonic horns (counterpart welding tools) 6 that are provided on the sheet holding drum 5; six anvil units 7 that ultrasonically weld the sheet W, between the ultrasonic horns 6 and respective anvil units 7; a cylindrical anvil holding drum 8 (see FIG. 3) that holds the anvil units 7; a cam drum 9 (see FIG. 3) provided inside the anvil holding drum 8; and six pressed members 18 (see FIG. 3) fixed to the sheet holding drum 5 and that are adjacent to respective ultrasonic horns 6.

Figure 3:
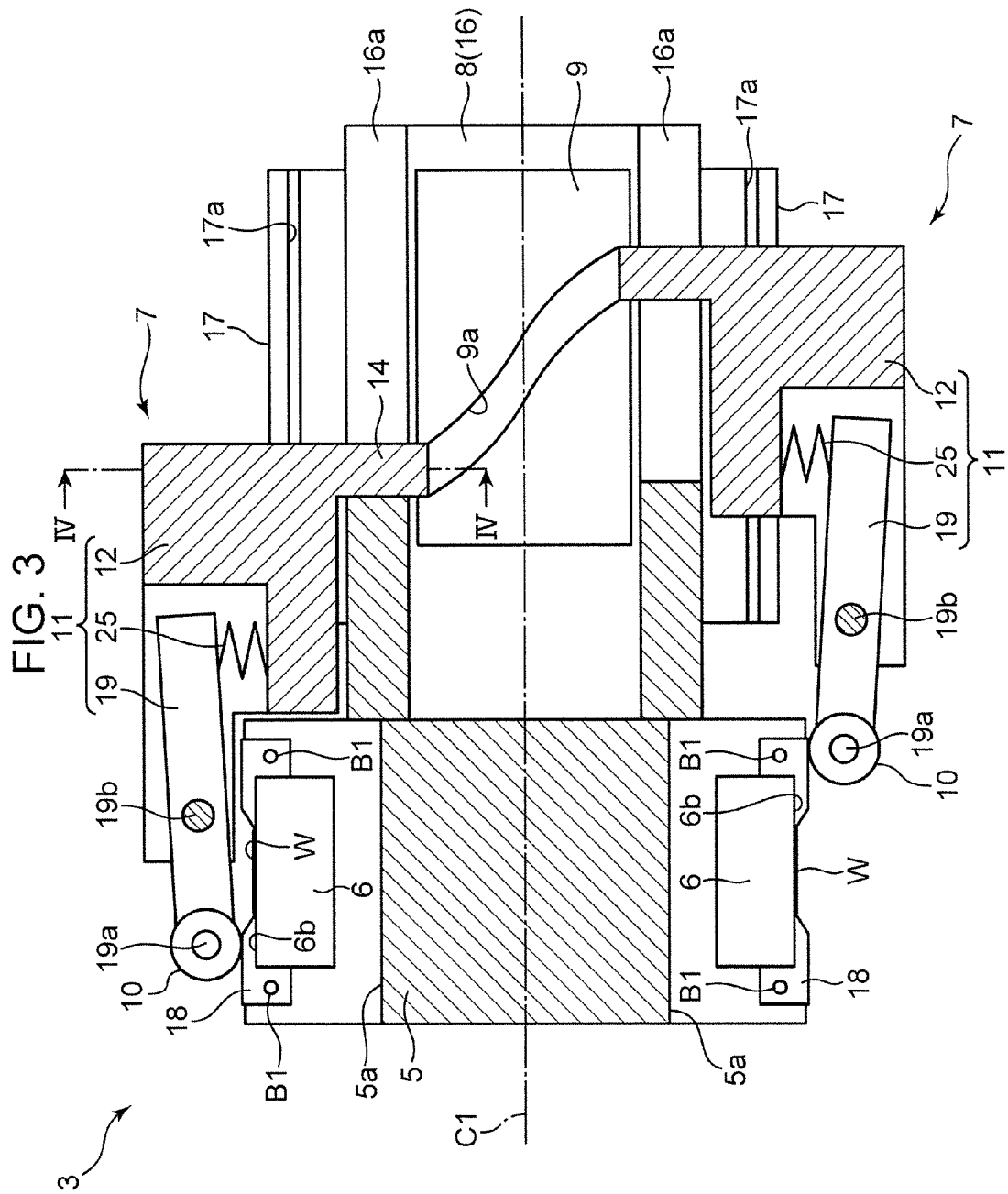
FIG. 3 is a cross-sectional diagram of FIG. 2 along line III-III.

With reference to FIG. 2 and FIG. 3, the sheet holding drum 5 can rotate about a rotation center C1 in a state where the sheet W is held on the outer peripheral surface of the sheet holding drum 5. Six recessed grooves 5a are formed equidistantly, about the rotation center C1, on the sheet holding drum 5. Each recessed groove 5a opens outward from the sheet holding drum 5 and extends along the rotation center C1.

The ultrasonic horns 6 apply ultrasonic vibration to the sheet W that is held by the sheet holding drum 5. The ultrasonic horns 6 have all the same configuration; accordingly, a single ultrasonic horn 6 alone will be explained, and a recurrent explanation of the remaining ultrasonic horns 6 will be omitted.

Figure 7:
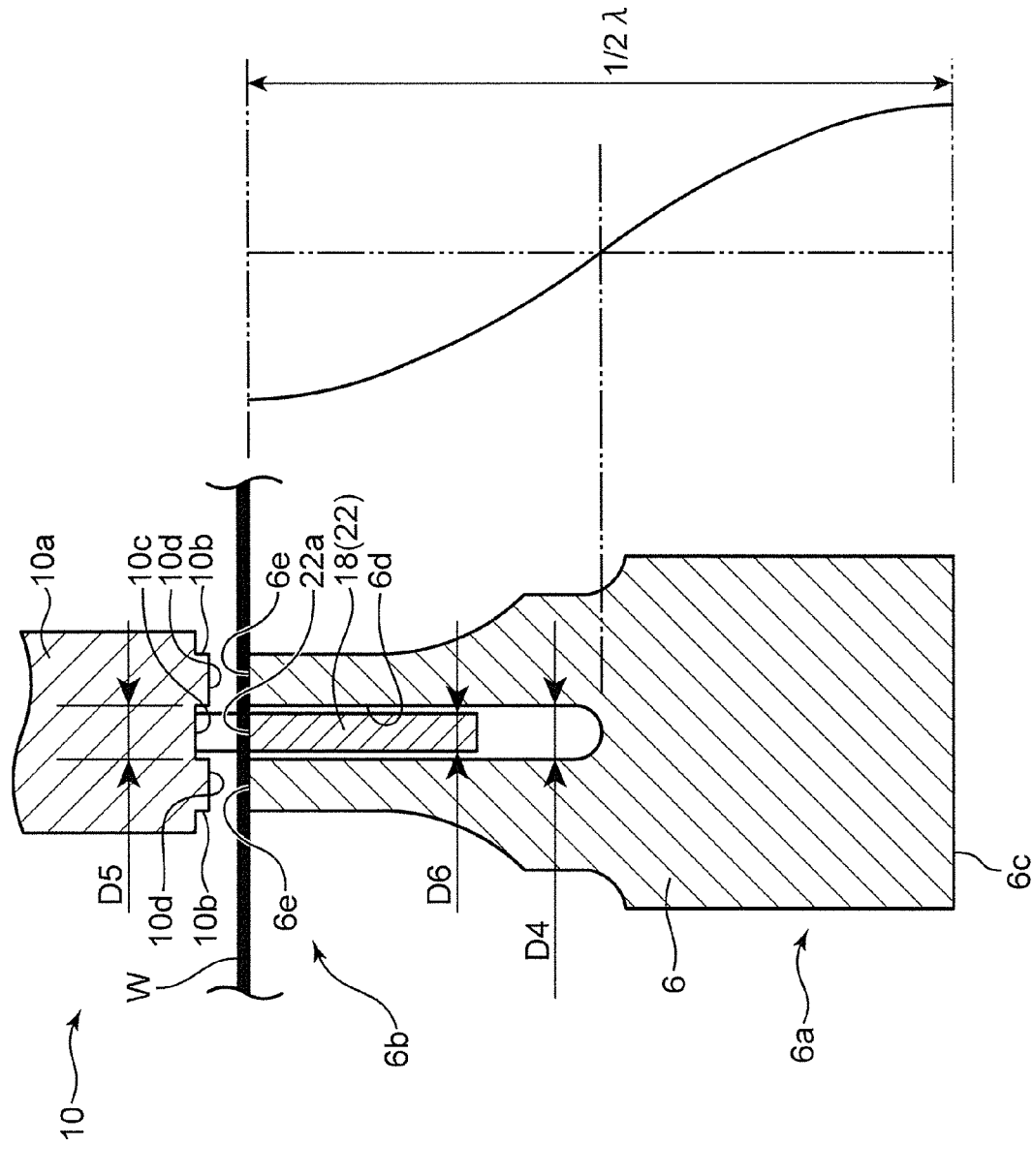
FIG. 7 is a cross-sectional diagram along line VII-VII of FIG. 6.

With reference to FIG. 7, each ultrasonic horn 6 is provided with an input-side end section 6a having an input surface 6c that receives ultrasonic vibration, and with an output-side end section 6b that is branched in a direction perpendicular to the rotation center C1 of the sheet holding drum 5, by a slit 6d that extends along the rotation center C1 (see FIG. 2), the output-side end section 6b having a pair of output surfaces 6e that output ultrasonic vibration on both sides of the slit 6d.

A width dimension D4 of the slit 6d is a dimension corresponding to the spacing D2 (see FIG. 1) of the two weld sections S that are welded simultaneously in the welding step P5.

The distance between the input surface 6c and the output surfaces 6e is set to a distance corresponding to a half-wavelength ($\frac{1}{2}\lambda$) of ultrasonic vibration that is input to the input surface 6c. The slit 6d is formed over a range from a position corresponding to a node of the ultrasonic vibration that is input to the input surface 6c, up to the end face (output surfaces 6e) of the output-side end section 6b.

The ultrasonic vibration that is input to the ultrasonic horn 6 are longitudinal waves in a direction perpendicular to the output surfaces 6e, but in the graph of FIG. 7, the ultrasonic vibration has been depicted as a transverse wave, for convenience in the explanation.

Figure 5:
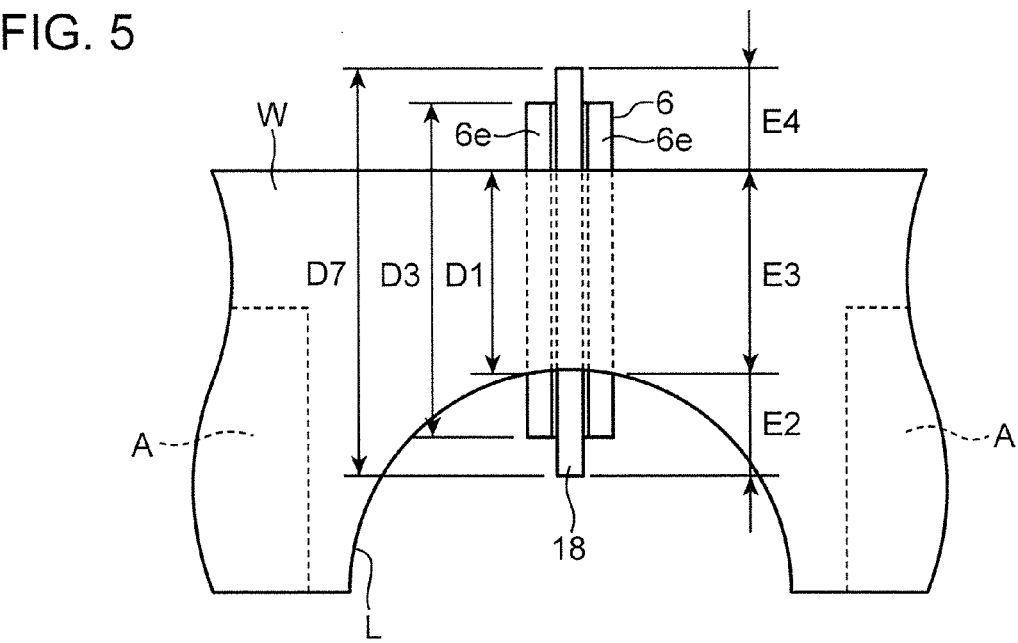
FIG. 5 is a diagram of the sheet holding drum of FIG. 3, viewed from outside.

As illustrated in FIG. 2 and FIG. 5, each ultrasonic horn 6 is provided within a respective recessed groove 5a in such a manner that the output surfaces 6e come in contact, from inside, with the sheet W that is held by the sheet holding drum 5.

As illustrated in FIG. 5, a length dimension D3 of the output surfaces 6e is longer than the welding area D1 set in the sheet W. The ultrasonic horn 6 is disposed in such a manner that both end sections of the output surfaces 6e, in the length direction, protrude beyond both sides of the welding area D1 (sheet W).

The anvil units 7 are provided at positions identical to those of the respective ultrasonic horns 6, about the rotation center C1. The anvil units 7 have the same configuration; hence, the configuration of just one of anvil unit 7 will be explained, while a recurrent explanation of the other anvil units 7 will be omitted.

Each anvil unit 7 is provided with an anvil roller (moving welding tool) 10 for welding the sheet W between a given ultrasonic horn 6 and the anvil roller 10, and with a holding member 11 that holds the anvil roller 10 in such a manner that the anvil roller 10 can move with respect to the sheet holding drum 5 along the rotation center C1.

Figure 4:
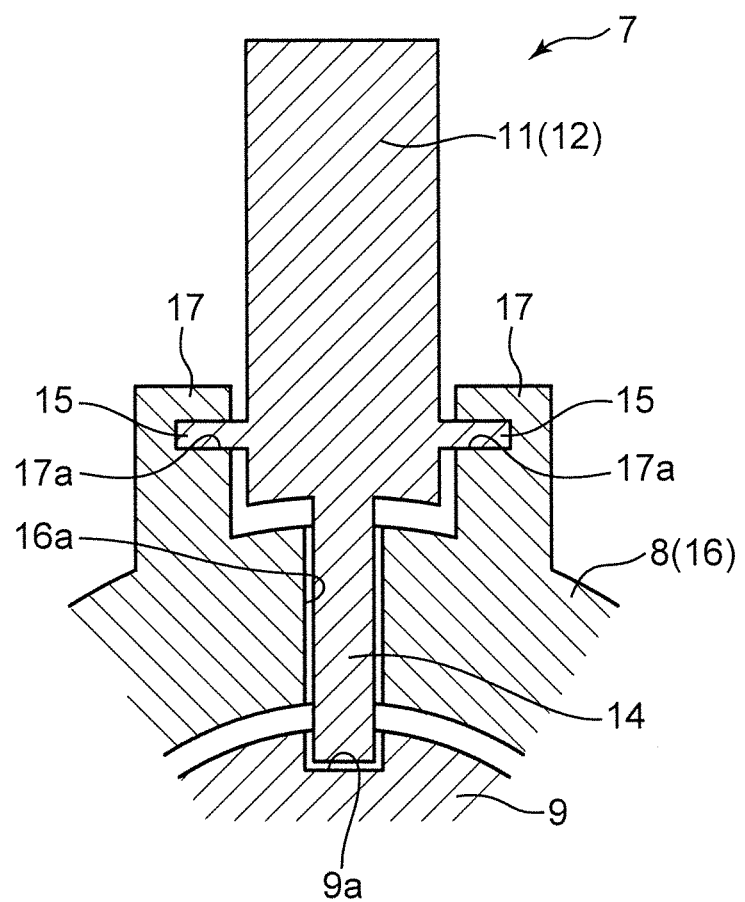
FIG. 4 is a cross-sectional diagram of FIG. 3 along line IV-IV.

As illustrated in FIG. 3 and FIG. 4, each holding member 11 is provided with: a holding member body 12 that is mounted so as to be movable along the rotation center C1 with respect to the anvil holding drum 8; a holding lever 19 that is pivotably mounted with respect to the holding member body 12 about a pivot shaft 19b, and that holds the anvil roller 10 in such a manner that the anvil roller 10 is rotatable about the rotary shaft 19a; and an urging member 25 that urges the holding lever 19 in a direction in which the anvil roller 10 moves close to the ultrasonic horn 6.

Herein, the rotary shaft 19a and the pivot shaft 19b are shafts that extend in a direction perpendicular to a plane that includes the rotation center C1 and the anvil unit 7 (a direction perpendicular to the paper in FIG. 3). The rotary shaft 19a is provided at a leading end section of the holding lever 19, and the pivot shaft 19b is provided at an intermediate section of the holding lever 19.

Accordingly, the anvil roller 10 can come into rolling contact with the sheet W in response to the movement of the holding member 11 along the rotation center C1, and can move close to or away from the sheet W (ultrasonic horn 6), in the radial direction of the sheet holding drum 5, in response to the swinging of the holding lever 19.

The urging member 25 urges the base end section of the holding lever 19 away from the rotation center C1, with respect to the holding member body 12; as a result, the anvil roller 10 is urged so as to draw close to the ultrasonic horn 6.

The urging member 25, the holding lever 19 and the pivot shaft 19b correspond to an urging mechanism that urges the anvil roller 10 toward the ultrasonic horn 6 in such a manner that the output surfaces 6e of the ultrasonic horn 6 and below-described welding surfaces 10d of the anvil roller 10 move closer in the normal direction thereof.

The holding member body 12 is provided with a cam protrusion 14 that extends toward the rotation center C1, and with a pair of engaging protrusions 15 that extend along the rotation center C1 and that protrude, in opposite orientations, in a direction (left-right direction in FIG. 4) that is perpendicular to the cam protrusion 14 and the rotation center C1.

The holding member body 12 is provided between a pair of rails 17 that are standed on the outer peripheral surface of the anvil holding drum 8. In the rails 17, engaging grooves 17a which open toward counterpart rails 17 and which extend along the rotation center C1 are formed. The engaging protrusions 15 of the holding member body 12 engage with respective engaging grooves 17a in such a manner that the engaging protrusions 15 can move, along the rotation center C1, with respect to anvil holding drum 8.

The cylindrical anvil holding drum 8 is provided with slits 16a that penetrate through the peripheral wall of the cylindrical anvil holding drum 8 and that extend along the rotation center C1. The cam protrusions 14 of the holding member body 12 are inserted into the anvil holding drum 8 via respective slits 16a.

The cam drum 9 is provided inside the anvil holding drum 8, and a cam groove 9a is formed in the outer peripheral surface of the cam drum 9. The leading end sections of the cam protrusions 14 are inserted into the cam groove 9a. The cam groove 9a guides the cam protrusions 14 in such a manner that the anvil units 7 move along the rotation center C1 in response to the rotation of the anvil holding drum 8 with respect to the cam drum 9.

The sheet holding drum 5 and the anvil holding drum 8 are fixed to each other and rotate integrally about the rotation center C1. By contrast, the rotational position of the cam drum 9 is fixed, regardless of the rotation of the sheet holding drum 5 and the anvil holding drum 8. Therefore, the holding member body 12 moves along the rotation center C1 in response to the rotation of the sheet holding drum 5 and the anvil holding drum 8 about the rotation center C1.

Specifically, the anvil unit 7 positioned lowermost in FIG. 2 and FIG. 3 is disposed at a position spaced, in a plan view, from the sheet W that is held by the sheet holding drum 5. In this state, the anvil unit 7 moves in a direction of coming close to the sheet W along the rotation center C1, in response to the counter-clockwise rotation, in FIG. 2, of the sheet holding drum 5.

In the process whereby the anvil unit 7 is displaced up to the topmost position in FIG. 2 and the FIG. 3, the anvil roller 10 crosses over the sheet W, and with the anvil unit 7 positioned topmost in FIG. 2 and the FIG. 3, the anvil roller 10 is disposed at a position spaced, in a plan view, from the sheet W that is held by the sheet holding drum 5. From this state, the sheet holding drum 5 further rotates counter-clockwise, whereupon the anvil roller 10 crosses over the sheet W once more and returns to a position of the anvil roller 10, being the lowermost position in FIG. 2 and FIG. 3.

In the ultrasonic welding device 1, thus, each anvil roller 10 reciprocates over the sheet W, in the welding area D1 of FIG. 1, within a range E1 of FIG. 2. The sheet W is welded during this reciprocating movement. In further detail, each anvil roller 10 positioned within a range outside the range E1 in FIG. 2 is positioned within a range E4 of FIG. 5, spaced from the sheet W in a plan view. When the anvil roller 10 enters the range E1, the anvil roller 10 moves sequentially over a range E3 that overlaps the sheet W in a plan view, a range E2 spaced from the sheet W in a plan view, on the side opposite that of the range E4, and then into the range E3.

The interiors of the range E4 and the range E2 correspond to a non-welding area, and the interior of the range E3 corresponds to a welding area. In the first to third embodiments hereafter the foregoing may be referred to as non-welding areas E2, E4 and welding area E3.

Figure 6:
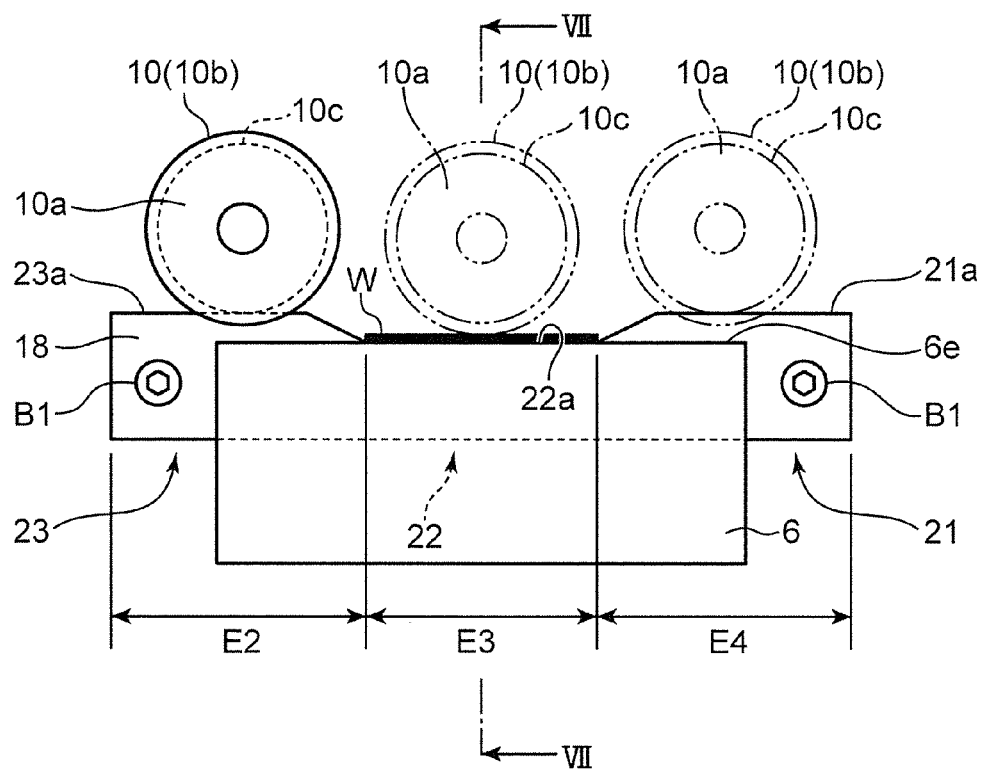
FIG. 6 is a side-view diagram illustrating an enlarged portion of FIG. 2.

An explanation follows next, with reference to FIG. 5 to FIG. 7, on the pressed members 18 for moving the anvil rollers 10, positioned within the non-welding areas E2, E4, away from the sheet W.

Each pressed member 18 has a width dimension D6 smaller than the width dimension D4 of the slit 6d of the ultrasonic horn 6, and is a plate-like member that is provided within the width-direction range of the slit 6d. The width dimension D6 of the pressed member 18 is smaller than the spacing D5 of a pair of protrusions 10b of the anvil roller 10. The protrusions 10b protrude, from the outer peripheral surface of a disk-shaped roller body 10a, over the entire circumference, and have respective welding surfaces 10d over which the sheet W is welded between the output surfaces 6e of the ultrasonic horn 6 and the welding surfaces 10d. The portion in the outer peripheral surface of the roller body 10a, between the protrusions 10b, constitutes a supported surface 10c that can come into rolling contact with the below-described pressed member 18.

The pressed member 18 has a length dimension D7 larger than the length dimension D3 of the ultrasonic horn 6, and is disposed along the rotation center C1. Specifically, both end sections of the pressed member 18 in the length direction are disposed outside the ultrasonic horn 6, and are fixed to the sheet holding drum 5 by way of a pair of bolts B1.

The pressed member 18 is provided with a base end-side guide section 21 disposed within the non-welding area E4, a central section 22 disposed within the welding area E3, and a leading end-side guide section 23 disposed within the non-welding area E2.

The central section 22 has a non-guide surface 22a disposed at a position flush with the output surfaces 6e of the ultrasonic horn 6, or closer to the rotation center C1 than the output surfaces 6e.

The base end-side guide section 21 has a base end-side guide surface 21a that includes an inclined surface that slants outward in the radial direction of the sheet holding drum 5 from the non-guide surface 22a toward a direction apart from the central section 22, and a flat surface that extends toward a direction apart from the central section 22 in a direction parallel to the non-guide surface 22a (output surfaces 6e), from the inclined surface.

Similarly, the leading end-side guide section 23 has a leading end-side guide surface 23a that includes an inclined surface that slants outward in the radial direction of the sheet holding drum 5 from the non-guide surface 22a toward a direction apart from the central section 22, and a flat surface that extends toward a direction apart from the central section 22 in a direction parallel to the non-guide surface 22a, from the inclined surface.

The two guide surfaces 21a, 23a correspond to a pressed surface against which the supported surface 10c of the anvil roller 10 positioned within the non-welding areas E2, E4 is pressed by the urging force of the urging mechanism (urging member 25, holding lever 19 and pivot shaft 19b). The pressed member 18 is fixed to the sheet holding drum 5 in a state where the two guide surfaces 21a, 23a are disposed within the width-direction range of the slit 16a.

The two guide surfaces 21a, 23a come into rolling contact with the supported surface 10c of the anvil roller 10 in response to the movement of the anvil roller 10 from the welding area E3 to the non-welding areas E2, E4; as a result, the anvil roller 10 that is positioned within the non-welding areas E2, E4 is drawn away from the sheet W (ultrasonic horn 6). The supported surface 10c is the outer peripheral surface (outer surface) of the roller body 10a that is positioned between the protrusions 10b of the anvil roller 10.

That is, the end section of the base end-side guide section 21 including the base end-side guide surface 21a, and the end section of the leading end-side guide section 23 including the leading end-side guide surface 23a, correspond to an inserted section that is inserted between the protrusions 10b of the anvil roller 10. Through insertion of the inserted section between the protrusions 10b, the pressed member 18 and the anvil roller 10 positioned within the non-welding areas E2, E4 engage each other so as to restrict the movement of the anvil roller 10 in a direction (left-right direction in FIG. 7) perpendicular to the movement direction of the anvil roller 10 and to the urging direction by the urging member 25.

The action of the anvil roller 10 by the pressed member 18 will be explained next.

In a process whereby the anvil roller 10 moves in the welding area E3, firstly, the welding surfaces 10d of the anvil roller 10 are pressed against the output surfaces 6e of the ultrasonic horn 6, in a state where the sheet W is sandwiched therebetween by the urging force by the urging member 25.

In this state, the sheet W is ultrasonically welded by applying ultrasonic vibration to the ultrasonic horn 6.

When the anvil roller 10 starts moving from the welding area E3 toward one of the non-welding areas E2, E4, the supported surface 10c of the anvil roller 10 abuts one of the inclined surfaces of the guide surfaces 21a, 23a. As the movement of the anvil roller 10 progresses, the anvil roller 10 comes into rolling contact with either guide surface 21a, 23a (inclined surface), and the anvil roller 10 moves gradually away from the ultrasonic horn 6, along the inclined surface, against the urging force by the urging member 25. As the anvil roller 10 moves further along, the anvil roller 10 is brought to a state of being supported by the flat surface of the guide surface 21a, 23a. That is, the two guide surfaces 21a, 23a have a shape that allows guiding the anvil roller 10 in a direction such that the output surfaces 6e and the welding surfaces 10d move away from each other in the normal direction thereof, against the urging force of the urging member 25.

In this state, the welding surfaces 10d of the anvil roller 10 move away from the output surfaces 6e of the ultrasonic horn 6 only by a predetermined dimension (dimension greater than the amplitude of ultrasonic vibration). It becomes accordingly possible to prevent wear and degradation of the ultrasonic horn 6 and of the anvil roller 10, caused by transmission, to the anvil roller 10, of the ultrasonic vibration that is applied to the ultrasonic horn 6.

Conversely, when the anvil roller 10 starts moving from the non-welding areas E2, E4 toward the welding area E3, the anvil roller 10 comes into rolling contact with the guide surface 21a, 23a, and is brought gradually closer to the ultrasonic horn 6, along the inclined surface, on account of the urging force by the urging member 25. The anvil roller 10 moves further along and reaches thereupon the welding area E3.

That is, the urging mechanism (urging member 25, holding lever 19 and pivot shaft 19b) and the pressed member 18 correspond to a displacement mechanism that displaces the anvil roller 10 with respect to the ultrasonic horn 6 in such a manner that the output surfaces 6e and the welding surfaces 10d approach each other in the welding area E3, and in such a manner that the output surfaces 6e and the welding surfaces 10d move away from each other in the non-welding areas E2, E4.

As explained above, the anvil roller 10 is urged toward the ultrasonic horn 6, and the outer surface of the anvil roller 10 that is positioned within the non-welding areas E2, E4 is pressed, on account of this urging force, against the guide surfaces 21a, 23a of the pressed member 18.

The anvil roller 10 can be guided, by the two guide surfaces 21a, 23a, in the direction in which the output surfaces 6e and the welding surfaces 10d move away from each other, in response to the movement of the anvil roller 10 from the welding area E3 to the non-welding areas E2, E4.

As a result, the output surfaces 6e and the welding surfaces 10d are moved closer in the normal direction of the surfaces by the urging force by the urging member 25, in a state where the anvil roller 10 has moved to the welding area E3, and the sheet W can be ultrasonically welded thereby between the output surfaces 6e and the welding surfaces 10d. The anvil roller 10 is guided along the guide surfaces 21a, 23a in response to the movement of the anvil roller 10 from the welding area E3 to the non-welding areas E2, E4; the output surfaces 6e and the welding surfaces 10d can thereby be caused to move away from each other.

Unlike in conventional instances, therefore, it becomes possible to dispense with structures (cylinder and structure that imparts drive power to the cylinder) for driving the anvil in the directions of moving close to or away from the ultrasonic horn, and to dispense with driving control of the anvil.

The guide surfaces 21a, 23a are provided between the pair of output surfaces 6e of the ultrasonic horn 6 (within the width-direction range of the slit 6d). Accordingly, the welding surfaces 10d of the anvil roller 10 can be caused to move reliably away from the output surfaces 6e, at a position in the immediate vicinity of the output surfaces 6e.

It becomes therefore possible to reliably prevent wear and degradation of the ultrasonic horn 6 and the anvil roller 10.

In the ultrasonic horn 6, the weight of the output-side end section 6b of the ultrasonic horn 6 is reduced by the slit 6d, and the output amplitude from the output surfaces 6e can be increased as a result.

The sheet W can therefore be ultrasonically welded more reliably.

The anvil roller 10 turns back at the non-welding areas E2, E4 positioned outside the welding area E3, and moves thereupon to the welding area E3. In a case where the sheet W is to be welded also at the turn-back points in the movement of the anvil roller 10, it is difficult to weld uniformly the sheet W in the movement direction, since ultrasonic energy is imparted to the sheet W both during deceleration and acceleration of the anvil roller 10. By contrast, welding can be carried out uniformly in the welding area E3 by setting the turn-back points of the anvil roller 10 to lie outside the welding area E3, as described above.

The ultrasonic welding device 1 according to the first embodiment elicits the following effects.

In the first embodiment, the output surfaces 6e and the welding surfaces 10d can be caused to move away from each other, in the normal direction thereof, by the guide surfaces 21a, 23a. It becomes accordingly possible to set the welding area E3 and the non-welding areas E2, E4, as appropriate, within the range of the output surfaces 6e, in the movement direction of the anvil roller 10.

In the first embodiment, the anvil roller 10 and the pressed member 18 at the non-welding areas E2, E4 can be positioned in a direction perpendicular to the movement direction of the anvil roller 10 and to the urging direction.

It becomes therefore possible to position the anvil roller 10 and the ultrasonic horn 6 prior to the movement of the anvil roller 10 to the welding area E3; as a result, welding can be carried out reliably between the ultrasonic horn 6 and the anvil roller 10 having moved to the welding area E3.

In the first embodiment, the pressed member 18 and the anvil roller 10 in the non-welding areas E2, E4 can be caused to engage each other using the supported surface 10c (region between the protrusions 10b) that does not contribute to welding of the sheet W, in the anvil roller 10.

In the first embodiment, the non-welding areas E2, E4 can be set at two sites that sandwiches the welding area E3. As a result, the sheet W can be welded reliably, while preventing wear and degradation of the anvil roller 10 and the ultrasonic horn 6, through the reciprocating movement of the anvil roller 10 between these two non-welding areas E2, E4.

According to the first embodiment, it is possible to reduce the weight of the ultrasonic horn 6 by the slit 6d, only at the portion of the ultrasonic horn 6 that is closer to the output surfaces 6e than the node of ultrasonic vibration is, and hence the output amplitude can be accordingly increased.

In the first embodiment, in particular, the reduction in the weight of the ultrasonic horn 6 by the slit 6d can be maximized since the slit 6d is formed over an area from the position corresponding to the node of ultrasonic vibration up to the end face (output surfaces 6e) of the output-side end section 6b.

The output amplitude can be effectively increased if the slit 6d is formed extending toward the end face of the output-side end section 6b from a position that is closer to the output surfaces 6e than the position corresponding to the node of ultrasonic vibration is.

In a production method using the ultrasonic welding device according to the first embodiment, the sheet W can be welded in a state where output amplitude has been increased through the use of the ultrasonic horn 6 that has the slit 6d, and the anvil roller 10 that is positioned within the non-welding areas E2, E4 can be caused to move away from the ultrasonic horn 6 by the pressed member 18 that is provided within the width range of the slit 6d.

Therefore, the anvil roller 10 that is positioned within the non-welding areas E2, E4 can be drawn away from the ultrasonic horn 6, while the sheet W is being reliably welded, with a large output amplitude; as a result, this allows preventing wear and degradation of the ultrasonic horn 6 and the anvil roller 10.

Two sites of a fold portion of the sheet W (weld sites of the two adjacent disposable diaper) are welded simultaneously by the pair of output surfaces 6e, and the sheet W is cut at a non-welding area (area between two weld sections S) of the sheet W, as defined by the slit 6d; the disposable diapers 20 can be produced as a result.

Second Embodiment

In the first embodiment, the guide surfaces 21a, 23a are provided in the pressed member 18, but a guide surface may be provided on at least one of the pressed member 18 and the anvil roller 10.

Figure 8:
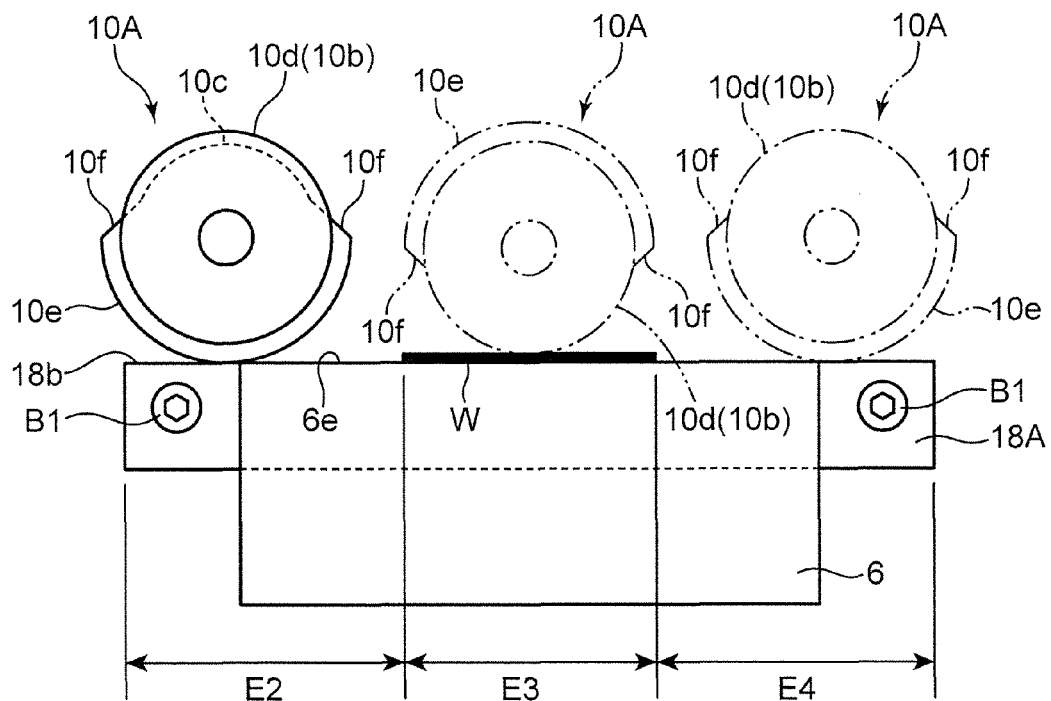
FIG. 8 is a diagram, corresponding to FIG. 6, illustrating an ultrasonic welding device according to a second embodiment of the present invention.

In an ultrasonic welding device according to a second embodiment, a guide surface (outer peripheral surface of a large-diameter section 10e) is provided in an anvil roller 10A, as illustrated in FIG. 8. A pressed member 18A according to the second embodiment has a flat surface 18b, provided flush with the output surfaces 6e of the ultrasonic horn 6, as a surface for rolling contact with the outer peripheral surface of a large-diameter section 10e of the anvil roller 10A.

The anvil roller 10A is provided with the large-diameter section 10e that protrudes from the supported surface 10c, between the pair of protrusions 10b.

The large-diameter section 10e is disposed concentrically with a cylindrical portion that defines the supported surface 10c, and is provided over an angle range of 180°. The outer peripheral surface of the large-diameter section 10e and the supported surface 10c are connected to each other by two inclined surfaces 10f.

In the second embodiment, half (90° range) the outer peripheral surface of the large-diameter section 10e and one of the inclined surfaces 10f constitute a guide surface for the non-welding area E2. The other half of the outer peripheral surface of the large-diameter section 10e and the other inclined surface 10f constitute a guide surface for the non-welding area E4.

In the process whereby the anvil roller 10A moves in the welding area E3, the welding surfaces 10d of the anvil roller 10A are pressed against the output surfaces 6e of the ultrasonic horn 6, in a state where the sheet W is sandwiched therebetween, on account of the urging force by the urging member 25, and comes into rolling contact with the sheet W.

In this state, the sheet W is ultrasonically welded by applying ultrasonic vibration to the ultrasonic horn 6.

When the anvil roller 10A starts moving from the welding area E3 toward the non-welding areas E2, E4, the inclined surfaces 10f of the anvil roller 10A abut the flat surface 18b of the pressed member 18. As the movement of the anvil roller 10A progresses further, the inclined surfaces 10f of the anvil roller 10A come into rolling contact with the flat surface 18b of the pressed member 18, and the welding surfaces 10d of the anvil roller 10A move gradually away from the output surfaces 6e of the ultrasonic horn 6, along the inclined surfaces 10f, against the urging force by the urging member 25. As the anvil roller 10A moves further along, the large-diameter section 10e of the anvil roller 10A is brought to a state of being supported by the flat surface 18b of the pressed member 18.

In the second embodiment as well, the welding surfaces 10d of the anvil roller 10A can be drawn away from the output surfaces 6e of the ultrasonic horn 6, against the urging force of the urging member 25, in response to the movement of the anvil roller 10A from the welding area E3 to the non-welding areas E2, E4.

At the outer peripheral surface of the large-diameter section 10e and at the flat surface 18b of the pressed member 18 there can be provided respective engaging sections that can engage each other in such a way so as to allow the movement of the anvil roller 10A to the welding area E3 and to restrict the movement of the anvil roller 10A in a direction perpendicular to the movement direction of the anvil roller 10A and to the urging direction by the urging member 25.

Third Embodiment

In the ultrasonic welding device according to the above embodiments, the ultrasonic horn 6 and the anvil roller 10 can be displaced relatively to each other, but it is also possible for both the ultrasonic horn 6 and the anvil roller 10 to be relatively displaced with respect to the sheet holding drum 5. That is, the ultrasonic horn 6, being a counterpart welding tool, may be relatively displaced with respect to the sheet holding drum 5.

Figure 9:
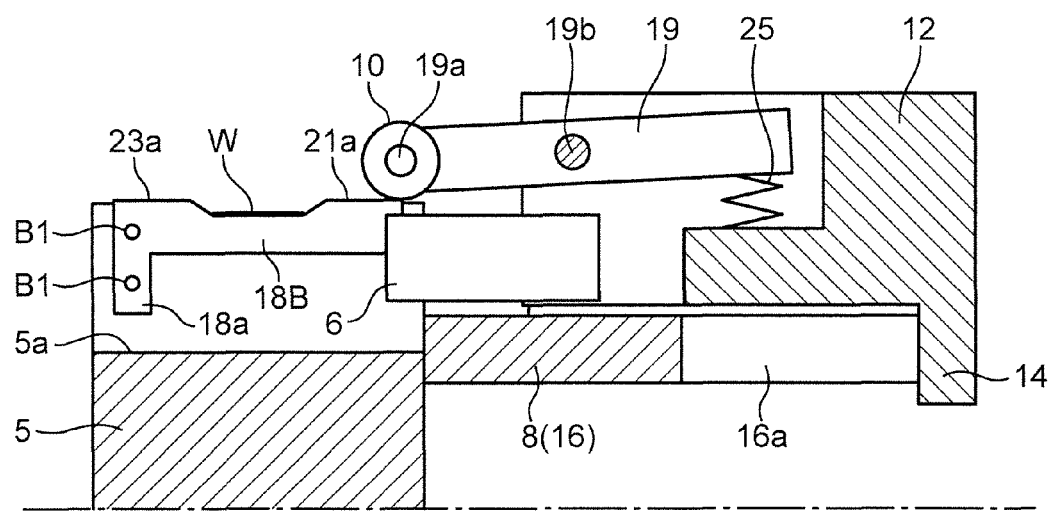
FIG. 9 is a lateral cross-sectional diagram of an ultrasonic welding device according to a third embodiment of the present invention.

As illustrated in FIG. 9, the ultrasonic horn 6 according to the third embodiment is held by the holding member body 12 of the anvil unit 7. Therefore, the ultrasonic horn 6 as well moves relatively with respect to the sheet holding drum 5 in response to the movement of the anvil unit 7.

In the third embodiment, the ultrasonic horn 6 and the pressed member 18B are displaced relatively to each other. FIG. 9 illustrates a state in which the anvil roller 10 has been displaced to the non-welding area E4; in this state, the end section of the pressed member 18B becomes inserted into the slit 6d of the ultrasonic horn 6.

Herein, the end section of the pressed member 18B that is always inserted in the slit 6d (end section on the right side of FIG. 9), constitutes a free end, while the end section 18a on the opposite side of the pressed member 18B is fixed by way of two bolts B1. The pressed member 18B can be reliably fixed to the sheet holding drum 5 as a result.

The feature wherein the guide surfaces 21a, 23a are provided in the pressed member 18B is identical to that of the first embodiment.

In the third embodiment as well, the welding surfaces 10d of the anvil roller 10 can be drawn away from the output surfaces 6e of the ultrasonic horn 6, in the normal direction of the foregoing surfaces, against the urging force of the urging member 25, in response to the movement of the anvil roller 10 from the welding area E3 to the non-welding areas E2, E4.

Fourth Embodiment

In the above embodiments there has been explained a pressed member 18 for drawing apart the output surfaces 6e and the welding surfaces 10d in the normal direction of the foregoing surfaces, but the pressed member may also serve the purpose of drawing the output surfaces 6e and the welding surfaces 10d apart in the movement direction of the anvil roller 10B.

Figure 10:
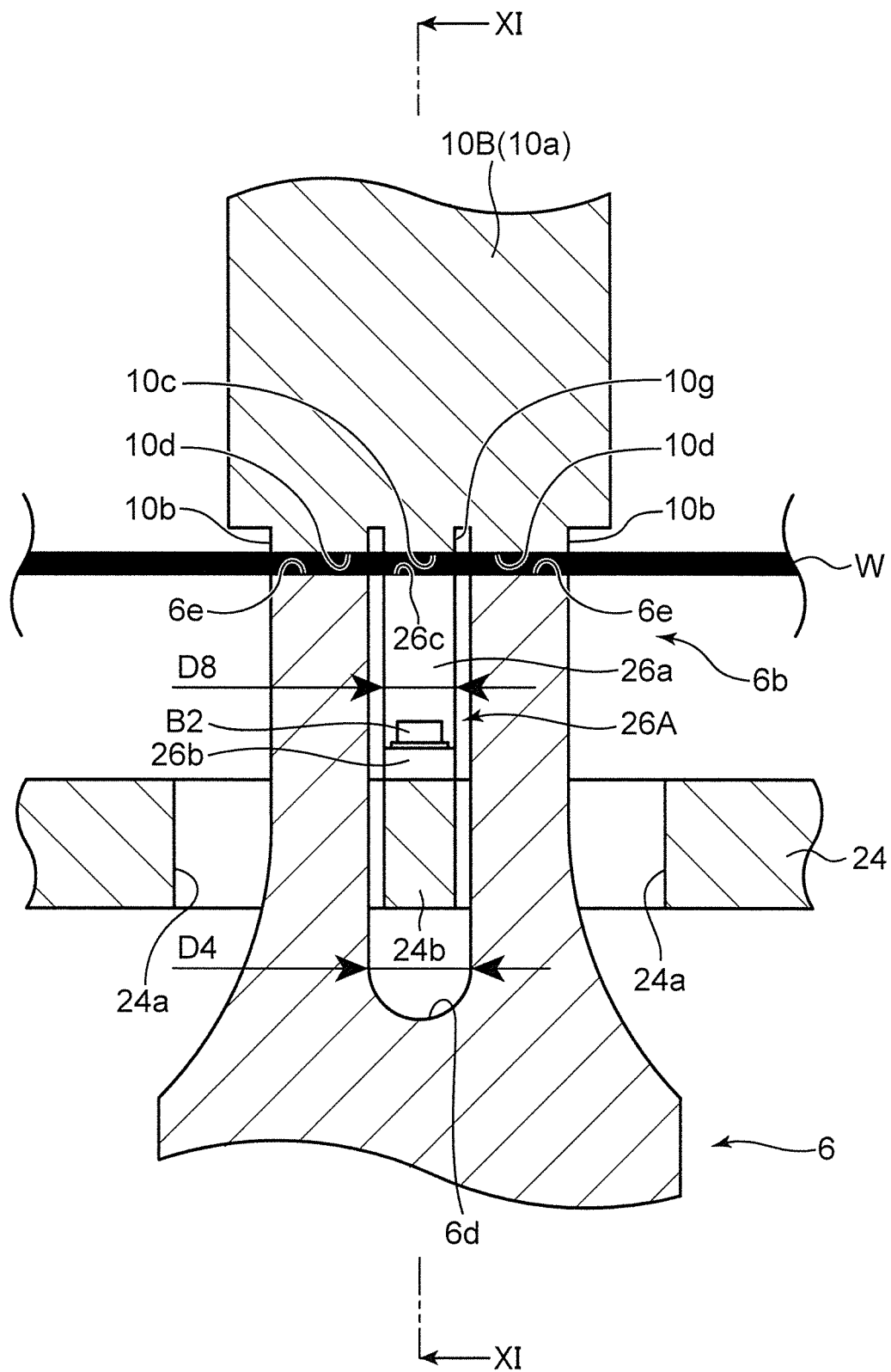
FIG. 10 is a diagram, corresponding to FIG. 7, illustrating an ultrasonic welding device according to a fourth embodiment of the present invention.
Figure 11:
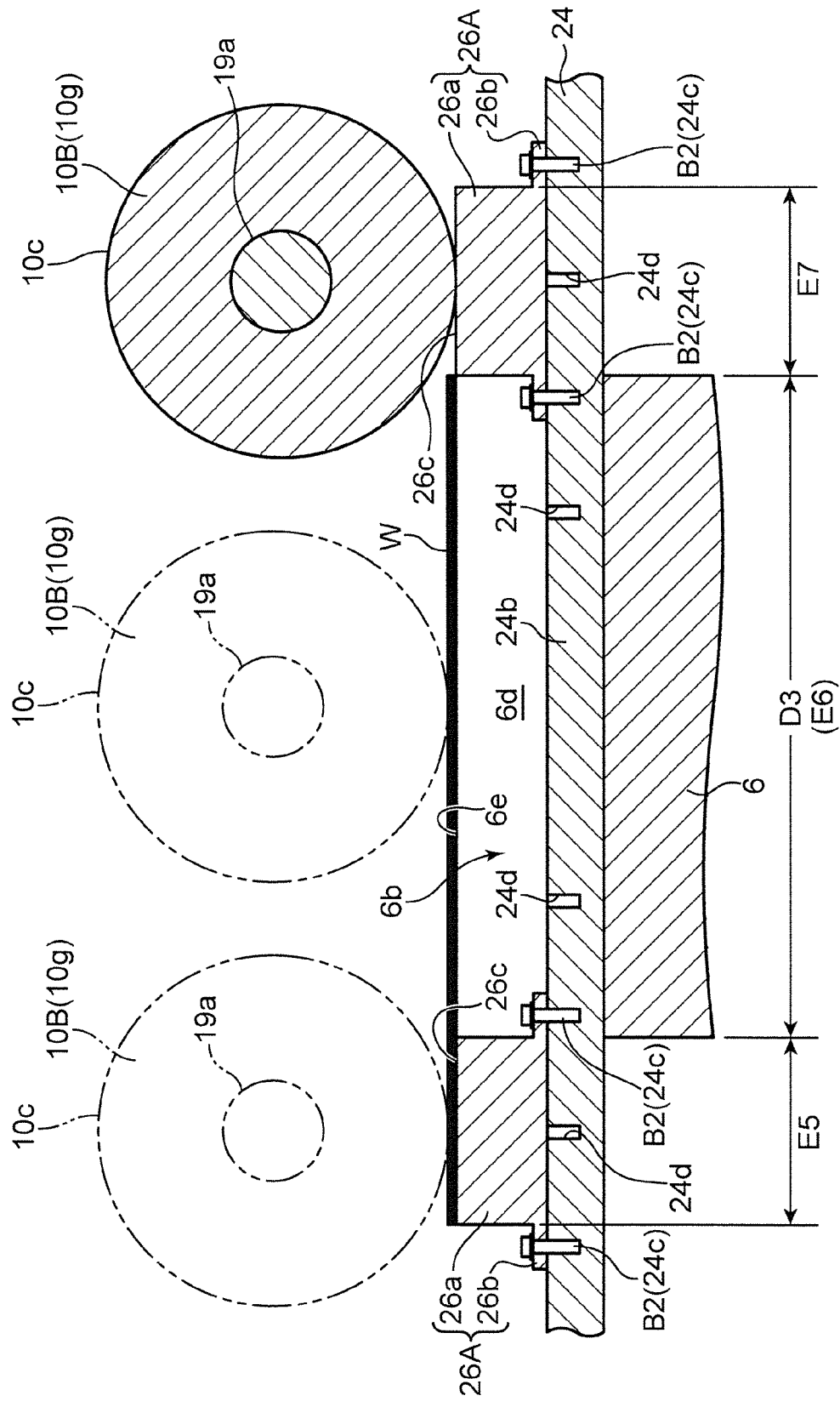
FIG. 11 is a cross-sectional diagram of FIG. 10 along line XI-XI.

An explanation follows next, with reference to FIG. 10 and FIG. 11, on an ultrasonic welding device according to a fourth embodiment. Features identical to those in the first and second embodiments will be denoted by the same reference symbols, and an explanation thereof will be omitted.

In the ultrasonic welding device according to the fourth embodiment there are set a welding area E6 identical to the length dimension D3 of the output surfaces 6e of the ultrasonic horn 6, and non-welding areas E5, E7 that are spaced from the welding area E6 in a plan view. FIG. 11 illustrates an example in which the sheet W is supplied so as to cover the welding area E6 and the non-welding area E5, but the sheet W may be supplied so as to cover at least the welding area E6.

The ultrasonic welding device is provided with a mounting plate 24 that is fixed to the sheet holding drum 5 (see FIG. 3) and with a pair of pressed members 26A that are mounted on the mounting plate 24.

The mounting plate 24 has a pair of insertion holes 24a for insertion of the portions, of the respective ultrasonic horns 6, that are branched by the slit 6d, and a passing section 24b that is positioned between the two insertion holes 24a and that passes between the branch portion of the ultrasonic horn 6.

The pressed members 26A in the pair thereof have the same configuration, and, accordingly, only the left pressed member 26A in FIG. 11 will be explained herein, while an explanation of the right pressed member 26A will be omitted.

The pressed member 26A has a guide surface 26c (pressed surface) that is pressed by the anvil roller 10B positioned within the non-welding area E5, on account of the urging force of the urging member 25 (FIG. 3).

Specifically, the pressed member 26A is provided with a body section 26a having the guide surface 26c, and with a pair of mounting sections 26b for mounting the body section 26a to the mounting plate 24. The pressed member 26A has a thickness dimension D8 smaller than the width dimension D4 of the slit 6d.

The body section 26a is a substantially rectangular plate-like portion that is fixed to the mounting plate 24 (sheet holding drum 5) in a state where the guide surface 26c is disposed within the width-direction range of the slit 6d. The body section 26a is mounted on the mounting plate 24 in such a manner that the guide surface 26c is continuous with the output surface of the ultrasonic horn 6, in the movement direction of the anvil roller 10B, and the guide surface 26c is disposed flush with the output surfaces 6e of the ultrasonic horn 6. Specifically, the body section 26a is disposed so as to extend in a direction apart from the ultrasonic horn 6, from the end face of the ultrasonic horn 6, in the side view illustrated in FIG. 11.

The pressed member 26A may be mounted to the mounting plate 24 in a state where part of the guide surface 26c enters between the slits 6d of the ultrasonic horn 6. Conversely, a clearance may be provided, between the guide surface 26c and the output surfaces 6e, such that the anvil roller 10B can move smoothly over the guide surface 26c and the output surfaces 6e.

The pair of mounting sections 26b is provided on both sides of the body section 26a and protrudes from the body section 26a in the movement direction of the anvil roller 10B. One of the mounting sections 26b is disposed in the slit 6d of the ultrasonic horn 6, and the other mounting section 26b is disposed outside the slit 6d. Insertion holes (reference symbol omitted) for insertion of bolts B2 are formed in the mounting sections 26b. The leading end sections of the bolts B2 that pass through these insertion holes are screwed into screw holes 24d of the mounting plate 24. The pressed member 26A can be mounted to the mounting plate 24 as a result.

As illustrated in FIG. 10, the anvil roller 10B according to the fourth embodiment has a supported section 10g having the same radius as that of the protrusions 10b. Specifically, the supported section 10g protrudes outward, in the radial direction, from the roller body 10a, between the pair of protrusions 10*b*. The outer peripheral surface (outer surface) of the supported section 10*g* functions as the supported surface 10*c* that is pressed against the guide surface 26*c* of the pressed member 26A.

The welding surfaces 10*d* of the anvil roller 10B positioned within the welding area E6 are pressed against the output surfaces 6*e* of the ultrasonic horn 6, on account of the urging force of the urging member 25, and the sheet W is welded between the welding surfaces 10*d* and the output surfaces 6*e*. The supported surface (outer surface) 10*c* of the anvil roller 10B that is positioned within the non-welding areas E5, E7 is pressed, on account of the urging force of the urging member 25, against the guide surface 26*c* or the sheet W. When the anvil roller 10B moves from the welding area E6 toward the non-welding areas E5, E7, the welding surfaces 10*d* move away from the output surfaces 6*e*, in the movement direction of the anvil roller 10B.

In the fourth embodiment, thus, the anvil roller 10B can be guided, in the movement direction thereof, when the anvil roller 10B moves up to a position spaced from the ultrasonic horn 6. As a result, the output surfaces 6*e* and the welding surfaces 10*d* can be drawn away from each other in the movement direction of the anvil roller 10B.

Figure 12:
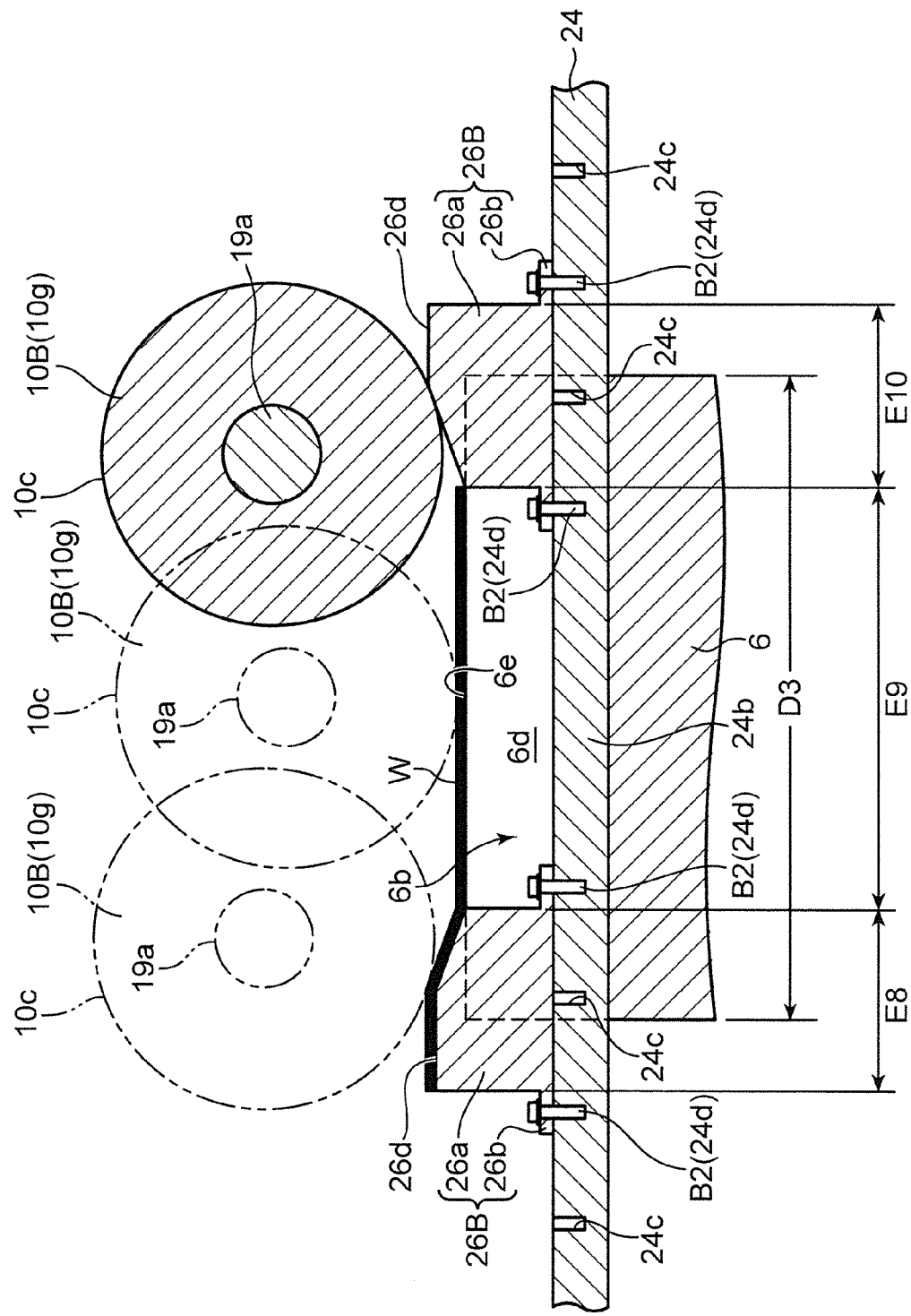
FIG. 12 is a cross-sectional diagram illustrating a state in which a pressed member of FIG. 11 has been replaced by another pressed member.

In the ultrasonic welding device according to the fourth embodiment, the welding areas can be switched between the welding area E6 and the non-welding areas E5, E7 illustrated in FIG. 11, and the welding area E9 and the non-welding areas E8, E10 illustrated in FIG. 12. The welding area E9 is set within the range of the length dimension D3 of the ultrasonic horn 6.

With reference to FIG. 12, the ultrasonic welding device has the pair of pressed members 26B having a guide surface 26*d* that has a shape different from that of the pressed members 26A described above. The two pressed members 26B have the same configuration, and hence only the pressed member 26B for defining the non-welding area E8 will be explained herein. The pressed member 26B has the same configuration as that of the pressed member 26A described above except for the guide surface 26*d*, and, accordingly, only the guide surface 26*d* will be explained.

The guide surface 26*d* has an inclined surface that slants outward in the radial direction of the sheet holding drum 5 from the welding area E9 toward the non-welding area E8, and a flat surface that extends in a direction parallel to the output surfaces 6*e* from the inclined surface toward a direction apart from the welding area E9. The welding surfaces 10*d* are guided by the guide surface 26*d* in a direction of moving away from the output surfaces 6*e* in the normal direction thereof against the urging force of the urging member 25 in response to the movement of the anvil roller 10B from the welding area E9 to the non-welding area E8 or the non-welding area E10.

The mounting plate 24 allows mounting the pressed members 26A, 26B at the two mounting positions set at different positions in the movement direction of the anvil roller 10B.

Specifically, the mounting plate 24 has a pair of outer screw holes 24*c* for mounting the pressed members 26A, and a pair of inner screw holes 24*d* for mounting the pressed members 26B.

As illustrated in FIG. 12, the bolts B2 that pass through the insertion holes of the mounting sections 26*b* of the pressed members 26B are screwed into the inner screw holes 24*d*; as a result, the pressed members 26B can be mounted to the mounting plate 24 in such a manner that the welding area E9 and the non-welding areas E8, E10 are defined thereby.

In a state where the pressed members 26B have been removed, meanwhile, the bolts B2 that pass through the insertion holes of the mounting sections 26*b* of the pressed members 26A are screwed into the outer screw holes 24*c*, as illustrated in FIG. 11; as a result, the pressed members 26A can be mounted to the mounting plate 24 in such a manner that the welding area E6 and the non-welding areas E5, E7 are defined thereby.

As a result, an ultrasonic welding device can be provided that allows producing a plurality of disposable diapers 20 having different welding areas.

The mutual pitch between the outer screw holes 24*c* and the mutual pitch between the inner screw holes 24*d* are set to be identical to each other, and the distances from the mounting sections 26*b* up to the end sections of the guide surfaces 26*c*, 26*d* in the two pressed members 26A, 26B are likewise set to be identical. As a result, it becomes possible to mount the pressed members 26B to the mounting plate 24, using the outer screw holes 24*c*. In this case, the welding surfaces 10*d* move away from the output surfaces 6*e*, in the normal direction thereof, by virtue of the guide surfaces 26*d* of the pressed members 26B, in response to the movement of the anvil roller 10B from the welding area E6 to the non-welding areas E5, E7. In this case, a single type of pressed member 26B allows switching between the welding area E6 and the welding area E9. The mounting section that allows mounting of the pressed members 26A, 26B to the sheet holding drum 5 (mounting plate 24) may be provided in at least one of the pressed members 26A, 26B and the sheet holding drum 5 (mounting plate 24) in such a way so as to enable continuous adjustment of the mounting position of the pressed members 26A, 26B in the movement direction of the anvil roller 10B.

Figure 13:
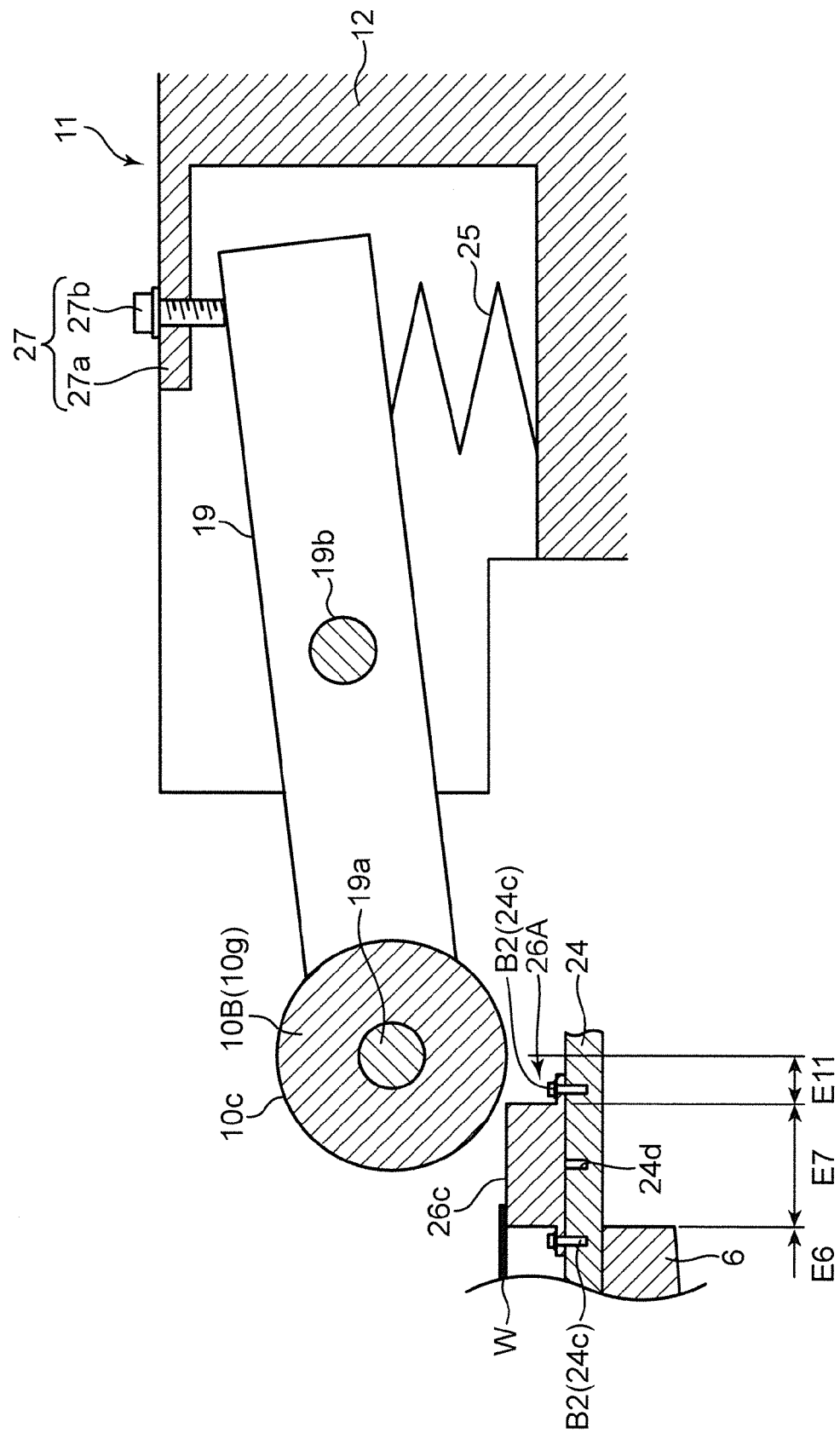
FIG. 13 is a cross-sectional diagram illustrating a movement restriction mechanism that is provided in the ultrasonic welding device illustrated in FIG. 10.
Figure 14:
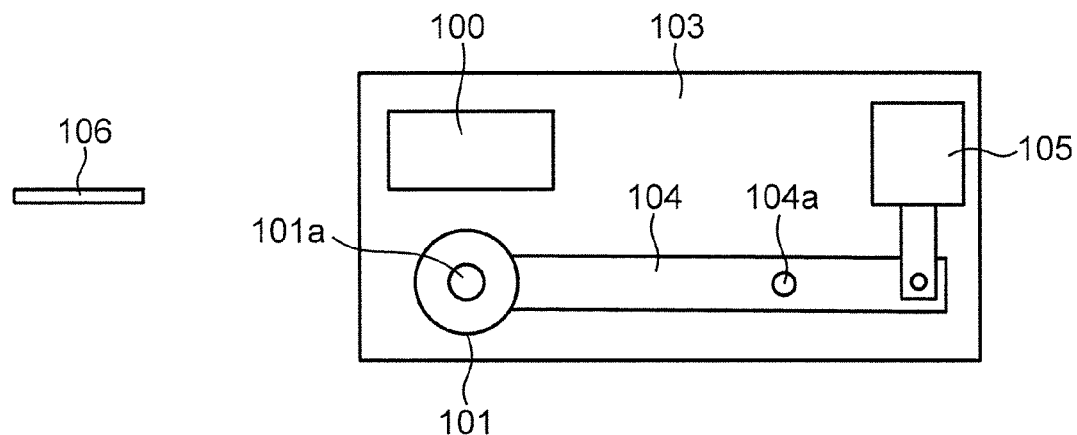
FIG. 14 is a schematic diagram illustrating an enlarged portion of a conventional ultrasonic welding device, depicted in a state where an anvil roller is in a non-welding area.
Figure 15:
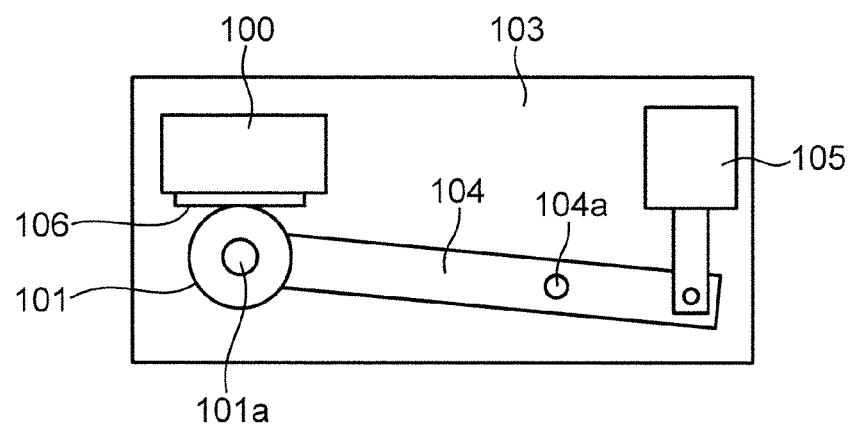
FIG. 15 is a schematic diagram of the ultrasonic welding device illustrated in FIG. 14, depicting a state in which an anvil roller is positioned within a welding area.

As illustrated in FIG. 13, it becomes possible to set a free range E11 at which the anvil roller 10B is not pressed against the pressed member 26A outside the non-welding area E7 described above. In this case, preferably, there is provided a holding mechanism 27 for maintaining the height position of the anvil roller 10B, having moved up to the free range E11, at a position that allows the anvil roller 10B to return on the guide surfaces 26*c*, 26*d*.

The holding mechanism 27 is provided with a bracket 27*a* provided on the holding member body 12 (see FIG. 3) and a stopper bolt 27*b* that penetrates through the bracket 27*a*, in the up-down direction.

The stopper bolt 27*b* is provided at a position at which the stopper bolt 27*b* can abut the base end section of the holding lever 19 that has moved to a predetermined height position in response to the rotation of the holding lever 19 about the pivot shaft 19*b*. The height position at which the stopper bolt 27*b* abuts the holding lever 19 can be adjusted through adjustment of the tightness of the stopper bolt 27*b* in a screw hole (reference symbol omitted) that is formed in the bracket 27*a*.

The height position of the anvil roller 10B that is maintained by the stopper bolt 27*b* is set to be identical to, or slightly lower than, the height position of the anvil roller 10B that is positioned within the welding area E6.

The anvil roller 10B can thus be held in a state of not being pressed against the pressed member 26A, 26B, within the free range E11. As a result, this facilitates for instance replacement of the anvil roller 10B.

The present invention is not limited to the embodiments described above, and may also adopt for instance the following forms.

In the above embodiments, the anvil roller 10 has been illustrated as the moving welding tool, and the ultrasonic horn 6 has been illustrated as the counterpart welding tool, but it is also possible to configure the ultrasonic welding device with the ultrasonic horn as the moving welding tool and with the anvil as the counterpart welding tool.

That is, the ultrasonic horn can be mounted on the sheet holding drum 5 in such a manner that the ultrasonic horn can move between the welding area and the non-welding areas with respect to the sheet holding drum 5.

In this case, the end section, of the counterpart welding tool (anvil), including the welding surfaces, is provided with a slit for branching of the end section. Direct contact between the ultrasonic horn and the pressed member is undesirable. Preferably, therefore, the portion for supporting the ultrasonic horn with respect to the sheet holding drum 5 is pressed against the pressed member.

The counterpart welding tool (anvil) may be fixed to the sheet holding drum 5, as in the first embodiment, but may be mounted so as to be movable with respect to the sheet holding drum 5, as in the third embodiment.

In all the embodiments described above, the welding tool that can move with respect to the sheet holding drum 5 (sheet W) is preferably formed by a roller that can come into rolling contact with the sheet W and the pressed member in response to the movement of the welding tool.

In the above first to third embodiments, one respective pressed member 18, 18A, 18B has been explained that extends over the non-welding area E2, the welding area E3 and the non-welding area E4, but the pressed member may be provided at least within an area corresponding to the non-welding area, as in the fourth embodiment.

For instance, one pressed member may be provided within an area corresponding to the non-welding area E2, and another pressed member may be provided within an area corresponding to the non-welding area E4. In a case where only one non-welding area is set, one guide member may be provided therein.

The features of the first to fourth embodiments may be combined with each other.

In the ultrasonic welding device of the fourth embodiment, specifically, the anvil roller 10B and the pressed members 26A, 26B may engage each other in such a manner that the movement of the anvil roller 10B is restricted in a direction perpendicular to the movement direction of the anvil roller 10B and perpendicular to the urging direction by the urging member 25.

The specific embodiments described above include an invention having the following features.

In order to solve the above problem, the present invention provides an ultrasonic welding device for ultrasonically welding an object to be welded, the ultrasonic welding device including: a holding member that holds an object to be welded; a pair of welding tools having an ultrasonic horn that has an output surface that applies ultrasonic vibration to the object to be welded, and an anvil having a welding surface over which the object to be welded is welded between the output surface of the ultrasonic horn and the anvil, the pair of welding tools being configured such that a moving welding tool that is one of the pair of welding tools can move, with respect to the holding member, over a welding area at which the output surface or the welding surface of the moving welding tool overlaps, in a plan view, the object to be welded that is held by the holding member, and over which the object to be welded is welded between the moving welding tool and a counterpart welding tool that is the other of the pair of welding tools, and a non-welding area that is spaced from the welding area in a plan view; and a displacement mechanism that displaces the moving welding tool with respect to the counterpart welding tool, in such a manner that the output surface and the welding surface approach each other in the welding area, and the output surface and the welding surface move away from each other in the non-welding area, wherein an end section of the counterpart welding tool including the output surface or the welding surface is branched, in a direction perpendicular to a movement direction of the moving welding tool, by a slit that extends in the movement direction, and has a pair of end faces positioned on both sides of the slit and functioning as the output surface or the welding surface, the displacement mechanism includes an urging mechanism that urges the moving welding tool toward the counterpart welding tool, in such a manner that the output surface and the welding surface move closer in the normal direction thereof, and a pressed member that has a pressed surface against which an outer surface of the moving welding tool, positioned within the non-welding area, is pressed by an urging force of the urging mechanism, the pressed member being fixed to the holding member in a state where the pressed surface is disposed within a width-direction range of the slit, and at least one of the pressed surface of the pressed member and the outer surface of the moving welding tool functions as a guide surface which, in response to the movement of the moving welding tool from the welding area to the non-welding area, guides the moving welding tool in a direction in which the output surface and the welding surface move away from each other.

In the present invention, the moving welding tool is urged toward the counterpart welding tool, and the outer surface of the moving welding tool that is positioned within the non-welding area is pressed, by this urging force, against the pressed surface of the pressed member.

At least one of the foregoing surfaces functions as a guide surface; as a result, it becomes possible to guide the moving welding tool, in response to the movement of the moving welding tool from the welding area to the non-welding area, in the direction in which the output surface and the welding surface move away from each other.

As a result, the output surface and the welding surface are moved closer in the normal direction of the surfaces by the urging force of the urging mechanism, in a state where the moving welding tool has moved to the welding area, and the object to be welded can be ultrasonically welded thereby between the output surface and the welding surface. The moving welding tool is guided along the guide surface, in response to the movement of the moving welding tool from the welding area to the non-welding area; the output surface and the welding surface can thereby be caused to move away from each other.

Unlike in conventional instances, therefore, the present invention allows to dispense with structures (cylinder and structure that imparts drive power to the cylinder) for driving the anvil in the directions of moving close to or away from the ultrasonic horn, and to dispense with driving control of the anvil.

In the present invention, further, the pressed surface is provided between the pair of end faces of the counterpart welding tool (within the width-direction range of the slit). Accordingly, the moving welding tool can be reliably drawn away from the end faces of the counterpart welding tool, at a position in the immediate vicinity of the end faces.

It becomes therefore possible to reliably prevent wear and degradation of the ultrasonic horn and the anvil.

In the present invention, the moving welding tool can move over the welding area and the non-welding area. The non-welding area is positioned herein spaced from the welding area in a plan view. That is, the moving welding tool turns back at the non-welding area positioned outside the welding area, and moves thereupon to the welding area.

In a case where the object to be welded is to be welded also at turn-back points in the movement of the moving welding tool, it is difficult to weld uniformly the object to be welded in the movement direction, since ultrasonic energy is imparted to the object to be welded both during deceleration and acceleration of the moving welding tool. By contrast, welding can be carried out uniformly in the welding area by setting the turn-back points of the moving welding tool to lie outside the welding area, as in the present invention.

In the present invention, the feature "pressed surface within the width-direction range of the slit" signifies that the pressed surface is disposed outside the slit, in the inner direction of the slit (movement direction of the moving welding tool) or the depth direction of the slit.

In the present invention, the feature "(pressed surface) against which an outer surface of the moving welding tool, positioned within the non-welding area, is pressed by an urging force of an urging mechanism" includes also an instance where the outer surface of the moving welding tool is pressed against the pressed surface in a state where the object to be welded is present between the pressed surface and the outer surface of the moving welding tool.

In the ultrasonic welding device, preferably, the guide surface has a shape that allows guiding the moving welding tool in the direction in which the output surface and the welding surface move away from each other in the normal direction thereof, against the urging force of the urging mechanism.

According to this aspect, the output surface and the welding surface can be caused to move away from each other in the normal direction thereof, by the guide surface. It becomes accordingly possible to set the welding area and the non-welding area, as appropriate, within the range of an output surface or a welding surface of the counterpart welding tool, in the movement direction of the moving welding tool.

In the ultrasonic welding device, preferably, the holding member has a pressed member mounting section that allows mounting the pressed member at a plurality of mounting positions that are set at different positions in the movement direction of the moving welding tool.

According to this aspect, the welding area and the non-welding area can be modified to a plurality of sites in the movement direction of the movement moving welding tool. Accordingly, an ultrasonic welding device can be provided that allows producing a plurality of articles having different welding areas.

In a case where the non-welding area is positioned at a position that is spaced from the output surface or the welding surface of the counterpart welding tool, in the movement direction of the moving welding tool, the guide surface may have a shape that allows guiding the moving welding tool in the direction in which the output surface and the welding surface move away from each other in the movement direction of the moving welding tool.

According to this aspect, the output surface and the welding surface can be caused to move away from each other, through guiding of the moving welding tool in the movement direction, in a case where the moving welding tool moves up to a position that is spaced from the counterpart welding tool.

In the ultrasonic welding device, preferably, the pressed member and the moving welding tool positioned within the non-welding area engage each other in such a manner as to allow the movement of the moving welding tool to the welding area, and restrict the movement of the moving welding tool in a direction perpendicular to the movement direction and to an urging direction by the urging mechanism.

According to this aspect, the pressed member and the moving welding tool positioned in the non-welding area can be positioned in a direction that is perpendicular to the movement direction of the moving welding tool and to the urging direction.

It becomes therefore possible to position the moving welding tool and the counterpart welding tool prior to the movement of the moving welding tool to the welding area; as a result, welding can be carried out reliably between the counterpart welding tool and the moving welding tool having moved to the welding area.

In the ultrasonic welding device, preferably, the moving welding tool is provided with a roller body having an outer surface that can come into rolling contact with the pressed member, and a pair of protrusions protruding outwardly from the roller body and welding the object to be welded between the pair of end faces of the counterpart welding tool and the pair of protrusions; and the pressed member has an inserted section that is inserted between the pair of protrusions of the moving welding tool positioned within the non-welding area.

According to this aspect, the pressed member and the moving welding tool positioned within the non-welding area can be caused to engage each other by utilizing the region (region between protrusions), in the moving welding tool, that does not contribute to welding of the object to be welded.

In the ultrasonic welding device, preferably, the ultrasonic welding device has two of the guide surfaces at respective positions on both sides of the welding area in the movement direction of the moving welding tool, in order to guide the moving welding tool in the direction in which the output surface and the welding surface move away from each other.

According to this aspect, two non-welding areas can be set at positions on both sides of the welding area. As a result, the object to be welded can be reliably welded, while preventing wear and degradation of the moving welding tool and the counterpart welding tool, through the reciprocating movement of the moving welding tool between the two non-welding areas.

In the ultrasonic welding device, preferably, the ultrasonic horn is the counterpart welding tool having an input-side end section that has an input surface that receives ultrasonic vibration, and an output-side end section having a pair of output surfaces that output ultrasonic vibration at respective positions on both sides of the slit; the distance between the input surface of the ultrasonic horn and each of the output surfaces of the ultrasonic horn is set to a distance corresponding to a half-wavelength of ultrasonic vibration that is input to the input surface; and the slit is formed over a range extending from a position corresponding to a node of ultrasonic vibration, or from a position that is closer to the output surfaces than the position corresponding to the node of ultrasonic vibration is, up to the end face of the output-side end section.

As is known, the output amplitude of an ultrasonic horn generally increases with decreasing ratio of the mass of the ultrasonic horn in a portion on the output surface side with respect to the mass of a portion on the input surface side, with reference to a node of the ultrasonic vibration that is input.

The above configuration allows reducing the weight of the ultrasonic horn by the slit, only at the portion of the ultrasonic horn that is closer to the output surface than the node of the ultrasonic vibration is. Therefore, the amplitude of the ultrasonic vibration that is output from the output surfaces (hereafter, output amplitude) can be accordingly increased.

In particular, the reduction in the weight of the ultrasonic horn afforded by the slit can be maximized in a case where the slit is formed over an area from the position corresponding to the node of ultrasonic vibration up to the end face of the output-side end section.

The "node" is a position at which the amplitude of the waveform of ultrasonic vibration becomes minimum (0).

Further, the present invention provides a method of producing a disposable diaper using the above ultrasonic welding device, the disposable diaper having a front abdominal section disposed on the abdomen of a wearer, a rear dorsal section disposed on the buttocks of the wearer, and a crotch section that extends from the front abdominal section, passing between the legs of the wearer, up to the rear dorsal section, the method having: a preparation step of preparing a continuous body in which constituent elements each constituted by connecting the front abdominal section and the rear dorsal section via the crotch section in a longitudinal direction are continuous in a transversal direction; a fold-in-half step of folding in half the continuous body in the longitudinal direction; a welding step of moving the moving welding tool over the welding area and the non-welding area and inputting ultrasonic vibration to the ultrasonic horn, to simultaneously weld two sites of an overlap portion in which a portion corresponding to a side edge portion of the front abdominal section and a portion corresponding to a side edge portion of the rear dorsal section are overlapped each other, in the continuous body, between a pair of end faces of the counterpart welding tool and an output surface or a welding surface of the moving welding tool; and a cutting step of cutting the continuous body between two weld sections formed in the welding step.

The production method according to the present invention allows bringing a moving welding tool, positioned within the non-welding area, away from the counterpart welding tool, by way of the pressed member that is provided within the width range of the slit.

According to the present invention, by causing the moving welding tool, positioned within the non-welding area, to move away from the counterpart welding tool, it possible to prevent wear and degradation of the moving welding tool and of the counterpart welding tool.

According to the present invention, two sites (weld sites of the two adjacent disposable diaper), in the continuous body, are welded simultaneously between the pair of end faces of the counterpart welding tool and the output surface or welding surface of the moving welding tool, and the continuous body is cut at a non-welding area of the continuous body, as defined by the slit (area between the two weld sections); the disposable diapers can be produced as a result.

The invention claimed is:

1. An ultrasonic welding device for ultrasonically welding an object to be welded, comprising:
   a holding member that holds an object to be welded;
   a pair of welding tools having an ultrasonic horn that has an output surface that applies ultrasonic vibration to the object to be welded, and an anvil having a welding surface over which the object to be welded is welded between the output surface of the ultrasonic horn and the anvil, the pair of welding tools being configured such that a moving welding tool that is one of the pair of welding tools can move, with respect to the holding member, over a welding area at which the output surface or the welding surface of the moving welding tool overlaps, in a plan view, the object to be welded that is held by the holding member, and over which the object to be welded is welded between the moving welding tool and a counterpart welding tool that is the other of the pair of welding tools, and a non-welding area that is spaced from the welding area in a plan view; and
   a displacement mechanism that displaces the moving welding tool with respect to the counterpart welding tool, in such a manner that the output surface and the welding surface approach each other in the welding area, and the output surface and the welding surface move away from each other in the non-welding area,
   wherein an end section of the counterpart welding tool including the output surface or the welding surface is branched, in a direction perpendicular to a movement direction of the moving welding tool, by a slit that extends in the movement direction, and has a pair of end faces positioned on both sides of the slit and functioning as the output surface or the welding surface,
   the displacement mechanism includes an urging mechanism that urges the moving welding tool toward the counterpart welding tool, in such a manner that the output surface and the welding surface move closer in the normal direction thereof, and a pressed member that has a pressed surface against which an outer surface of the moving welding tool, positioned within the non-welding area, is pressed by an urging force of the urging mechanism, the pressed member being fixed to the holding member in a state where the pressed surface is disposed within a width-direction range of the slit, and
   at least one of the pressed surface of the pressed member and the outer surface of the moving welding tool functions as a guide surface which, in response to the movement of the moving welding tool from the welding area to the non-welding area, guides the moving welding tool in a direction in which the output surface and the welding surface move away from each other.

2. The ultrasonic welding device according to claim 1, wherein the guide surface has a shape that allows guiding the moving welding tool in the direction in which the output surface and the welding surface move away from each other in the normal direction thereof, against the urging force of the urging mechanism.

3. The ultrasonic welding device according to claim 2, wherein the holding member has a pressed member mounting section that allows mounting the pressed member at a plurality of mounting positions that are set at different positions in the movement direction of the moving welding tool.

4. The ultrasonic welding device according to claim 1, wherein the non-welding area is set at a position that is spaced from the output surface or the welding surface of the counterpart welding tool in the movement direction of the moving welding tool, and
the guide surface has a shape that allows guiding the moving welding tool in the direction in which the output surface and the welding surface move away from each other in the movement direction of the moving welding tool.

5. The ultrasonic welding device according to claim 1, wherein the pressed member and the moving welding tool positioned within the non-welding area engage each other in such a manner as to allow the movement of the moving welding tool to the welding area, and restrict the movement of the moving welding tool in a direction perpendicular to the movement direction and to an urging direction by the urging mechanism.

6. The ultrasonic welding device according to claim 5, wherein the moving welding tool is provided with a roller body having an outer surface that can come into rolling contact with the pressed member, and a pair of protrusions protruding outwardly from the roller body and welding the object to be welded between the pair of end faces of the counterpart welding tool and the pair of protrusions; and the pressed member has an inserted section that is inserted between the pair of protrusions of the moving welding tool positioned within the non-welding area.

7. The ultrasonic welding device according to claim 1, wherein the ultrasonic welding device has two of the guide surfaces at respective positions on both sides of the welding area in the movement direction of the moving welding tool, in order to guide the moving welding tool in the direction in which the output surface and the welding surface move away from each other.

8. The ultrasonic welding device according to claim 1, wherein the ultrasonic horn is the counterpart welding tool having an input-side end section that has an input surface that receives ultrasonic vibration, and an output-side end section having a pair of output surfaces that output ultrasonic vibration at respective positions on both sides of the slit, the distance between the input surface of the ultrasonic horn and each of the output surfaces of the ultrasonic horn is set to a distance corresponding to a half-wavelength of ultrasonic vibration that is input to the input surface, and the slit is formed over a range extending from a position corresponding to a node of ultrasonic vibration, or from a position that is closer to the output surfaces than the position corresponding to the node of ultrasonic vibration is, up to the end face of the output-side end section.

9. A method of producing a disposable diaper using the ultrasonic welding device according to claim 1, the disposable diaper having a front abdominal section disposed on the abdomen of a wearer, a rear dorsal section disposed on the buttocks of the wearer, and a crotch section that extends from the front abdominal section, passing between the legs of the wearer, up to the rear dorsal section, the method comprising:
a preparation step of preparing a continuous body in which constituent elements each constituted by connecting the front abdominal section and the rear dorsal section via the crotch section in a longitudinal direction are continuous in a transversal direction;
a fold-in-half step of folding in half the continuous body in the longitudinal direction;
a welding step of moving the moving welding tool over the welding area and the non-welding area and inputting ultrasonic vibration to the ultrasonic horn, to simultaneously weld two sites of an overlap portion in which a portion corresponding to a side edge portion of the front abdominal section and a portion corresponding to a side edge portion of the rear dorsal section are overlapped each other, in the continuous body, between a pair of end faces of the counterpart welding tool and an output surface or a welding surface of the moving welding tool; and
a cutting step of cutting the continuous body between two weld sections formed in the welding step.

* * * * *